(12) United States Patent
Von Guggenberg Zu Riedhofen et al.

(10) Patent No.: US 12,049,518 B2
(45) Date of Patent: Jul. 30, 2024

(54) PHARMACOKINETICS AND CHOLECYSTOKININ-2 RECEPTOR (CCK2R) TARGETING FOR DIAGNOSIS AND THERAPY

(71) Applicant: Medizinische Universitat Innsbruck, Innsbruck (AT)

(72) Inventors: Elisabeth Von Guggenberg Zu Riedhofen, Innsbruck (AT); Maximilian Klingler, Innsbruck (AT)

(73) Assignee: Medizinische Universität Innsbruck, Innsbruck (AT)

( * ) Notice: Subject to any disclaimer, the term of this patent is extended or adjusted under 35 U.S.C. 154(b) by 63 days.

(21) Appl. No.: 16/620,403

(22) PCT Filed: Jun. 8, 2018

(86) PCT No.: PCT/EP2018/065206
§ 371 (c)(1),
(2) Date: Dec. 6, 2019

(87) PCT Pub. No.: WO2018/224665
PCT Pub. Date: Dec. 13, 2018

(65) Prior Publication Data
US 2021/0388025 A1    Dec. 16, 2021

(30) Foreign Application Priority Data
Jun. 8, 2017 (EP) .................... 17174973

(51) Int. Cl.
| C07K 7/08 | (2006.01) |
| A61K 38/08 | (2019.01) |
| A61K 51/08 | (2006.01) |
| C07K 7/06 | (2006.01) |
| A61K 38/00 | (2006.01) |

(52) U.S. Cl.
CPC ............... *C07K 7/08* (2013.01); *A61K 38/08* (2013.01); *A61K 51/088* (2013.01); *C07K 7/06* (2013.01); *A61K 38/00* (2013.01)

(58) Field of Classification Search
CPC ... C07K 7/00; C07K 7/08; C07K 7/06; C07K 14/595; A61K 38/08; A61K 38/10; A61K 38/16; A61K 38/2207; A61K 38/00
See application file for complete search history.

(56) References Cited

U.S. PATENT DOCUMENTS

| 2012/0231999 A1* | 9/2012 | Alagarsamy | A61P 35/00 514/4.8 |
| 2017/0008928 A1* | 1/2017 | Kruse | A61K 47/10 |

FOREIGN PATENT DOCUMENTS

| TW | 202231655 A | 8/2022 |
| TW | 202241926 A | 11/2022 |
| WO | 2015/067473 | 5/2015 |
| WO | 2017/005765 | 1/2017 |
| WO | 2018224665 A1 | 12/2018 |
| WO | 2019057445 A1 | 3/2019 |

OTHER PUBLICATIONS

Corringer et al. "CCK-B Agonist or Antagonist Activities of Structurally Hindered and Peptidase-Resistant Boc-CCK4 Derivatives", J. Med. Chem, 1993, 166-172 (Year: 193).*
Rao et al. "Characterization of SNF 9007, A Novel Cholecystokinin/Opoid Ligand in Mouse Ileum in Vitro: Evidence for Involvement of Cholecystokinin A and Cholecystokinin B Receptors in Regulation of Ion Transport1", The Journal of Pharmacology and Experimental Therapeutics, 1994, pp. 1003-1009 (Year: 1994).*
Roosenburg et al. Radiolabeled CCK/gastrin peptides for imaging and therapy of CCK2 receptor-expressing tumors, Amino Acids, 2011, 1049-1058 (Year: 2011).*
Roosenburg, "Radiolabeled CCK/gastrin peptides for imaging and therapy of CCK2 receptor-expressing tumors", Amino Acids, 2011 pp. 1049-1058 (Year: 2011).*
Good et al. "Macrocyclic chelator-coupled gastrin-based radiopharmaceuticals for targeting gastrin receptor-expressing tumours", Eur J Nucl Med Mol Imaging, 2008, pp. 1868-1877 (Year: 2008).*
Corringer et al. "CCK-B Agonist or Antagonist Activities of Structurally Hindered and Peptidase-Resistance Boc-CCK4 Derivatives", J. Med. Chem., 1993, pp. 166-172 (Year: 1993).*
International Search Report and Written Opinion of International Application No. PCT/EP2018/065206, mailed Sep. 17, 2018, 12 pages.
Corringer et al "CCK-B agonist or antagonist activities of structurally hindered and peptidase-resistant Boc-CCK4 derivatives" Journal of Medicinal Chemistry, 36(1):166-172 (1993).
Klingler et al "Site-specific stabilization of minigastrin analogs against enzymatic degradation for enhanced cholecystokinin-2 receptor targeting" Theranostics, 8(11):2896-2908 (2018).
Extended European Search Report corresponding to European Application No. 17174973.2, dated Sep. 25, 2017, 8 pages.
Klingler et al. "DOTA-MGS5, a New Cholecystokinin-2 Receptor-Targeting Peptide Analog with an Optimized Targeting Profile for Theranostic Use" The Journal of Nuclear Medicine, 60(7):1010-1016 (2019).
Zavvar et al. "Effects of Side Chain and Peptide Bond Modifications on the Targeting Properties of Stabilized Minigastrin Analogs" Pharmaceuticals, 16(278):1-17 (2023).

(Continued)

*Primary Examiner* — Lianko G Garyu
(74) *Attorney, Agent, or Firm* — Myers Bigel, P.A.

(57) ABSTRACT

The present invention provides valuable peptidomimetics for therapeutic and diagnostic purposes as well as compositions, methods, uses and kits based on these peptidomimetics. In particular, the peptidomimetics of the present invention are incorporated by CCK2R expressing cells, for instance, cancer cells. This allows, for instance, to selectively destroy cancer cells or to selectively image cancer cells that express CCK2R.

23 Claims, 8 Drawing Sheets

Specification includes a Sequence Listing.

(56) References Cited

OTHER PUBLICATIONS

"Ex Parte Eberhard Ammermann, Reinhard Stierl, Gisela Lorenz, Siegfried Strathmann, Klaus Schelberger, V. James Spadafora, and Thomas Christen", 2019 WL 6208282 (Patent Tr. & App. Bd.).
"Ex Parte Jan Wästlund-Karlsson, Patrik Krook, and Birgitta Yhlen", 2015 WL 4710492 (Patent Tr. & App. Bd.).
"Ex Parte Jean-Alex Laffitte and Vijay R. Srinivas", 2022 WL 485046 (Patent Tr. & App. Bd.).
"Ex Parte Masahiro Orihashi, Junpei Koike, and Kanako Masuda", 2010 WL 991526 (Bd.Pat.App. & Interf.).
"Ex Parte Mudge", 2010 WL 4670640 (Bd. Pat. App. & Interf. Nov. 16, 2010).
"Ex parte The NutraSweet Co.", 19 USPQ2d 1586 (Bd. Pat. App. & Inter. 1991), cited in the MPEP §716.02(a).
Boermann, Otto C, et al., "Evaluation of CCK2 receptor binding ligands: the inheritance of Thomas Behr", Eur J Nucl Med Mol Imaging 38:1407-1409 (Jun. 7, 2011).
Corringer, P. J, et al., "CCK-B Agonist or Antagonist Activities of Structurally Hindered and Peptidase-Resistant Boc-CCK, Derivatives", J. Med. Chem 36:166-172 (1993).
Good, Stephan, et al., "Macrocyclic chelator-coupled gastrin-based radiopharmaceuticals for targeting of gastrin receptor-expressing tumours", Eur J Nucl Med Mol Imaging 35:1868-1877 (May 29, 2008).
Kaloudi, Aikaterini, et al., "Impact of clinically tested NEP/ACE inhibitors on tumor uptake of [111 In-DOTA]MG11—first estimates for clinical translation", EJNMMI Research 6:15 (2016) 10 pages.
Kaloudi, Aikaterini, et al., "Improving the In Vivo Profile of Minigastrin Radiotracers: A Comparative Study Involving the Neutral Endopeptidase Inhibitor Phosphoramidon", Cancer Biotherapy and Radiopharmaceuticals 31(1):20-28 (2016).
Kaloudi, Aikaterini, et al., "In vivo inhibition of neutral endopeptidase enhances the diagnostic potential of truncated gastrin 111 In-radioligands", Nuclear Medicine and Biology 42:824-832 (2015).
Klinger, Maximilian, et al., "Site-specific stabilization of minigastrin analogs against enzymatic degradation for enhanced cholecystokinin-2 receptor targeting", Theranostics 8(11):2896-2908 (Apr. 16, 2018).
Laverman, Peter, et al., "Comparative biodistribution of 12 111 In-labelled gastrin/CCK2 receptor-targeting peptides", Eur J Nucl Med Mol Imaging 38:1410-1416 (Apr. 2, 2011).
Mather, Stephen J, et al., "Selection of Radiolabeled Gastrin Analogs for Peptide Receptor-Targeted Radionuclide Therapy", J Nucl Med 48:615-622 (2007).
Ocak, Meltem, et al., "Comparison of biological stability and metabolism of CCK2 receptor targeting peptides, a collaborative project under Cost BM0607", Eur J Nucl Med Mol Imaging 38:1426-1435 (Apr. 29, 2011).
Roosenburg, Susan, et al., "Radiolabeled CCK/gastrin peptides for imaging and therapy of CCK2 receptor- expressing tumors", Amino Acids 41:1049-1058 (Mar. 3, 2010).
Roosenburg, Susan, et al., "Stabilized 111 In-Labeled sCCK8 Analogues for Targeting CCK2-Receptor Positive Tumors: Synthesis and Evaluation", Bioconjugate Chem. 21:663-670 (Mar. 19, 2010).
Sauter, Alexander W, et al., "Targeting of the Cholecystokinin-2 Receptor with the Minigastrin Analog 177 Lu-DOTA-PP-F11N: Does the Use of Protease Inhibitors Further Improve In Vivo Distribution?", J Nucl Med 60:393-399 (Jul. 12, 2018).

* cited by examiner

A)

B)

C)

SEQUENCE LISTING

```
<160> NUMBER OF SEQ ID NOS: 18

<210> SEQ ID NO 1
<211> LENGTH: 8
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<223> OTHER INFORMATION: amidated at the C-terminus

<400> SEQUENCE: 1

Asp Tyr Met Gly Trp Met Asp Phe
1               5

<210> SEQ ID NO 2
<211> LENGTH: 13
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<223> OTHER INFORMATION: amidated at the C-terminus

<400> SEQUENCE: 2
```

```
Leu Glu Glu Glu Glu Glu Ala Tyr Gly Trp Met Asp Phe
1               5                   10
```

<210> SEQ ID NO 3
<211> LENGTH: 4
<212> TYPE: PRT
<213> ORGANISM: Artificial Sequence
<220> FEATURE:
<223> OTHER INFORMATION: amino acid polymer
<220> FEATURE:
<221> NAME/KEY: misc_feature
<222> LOCATION: (1)..(1)
<223> OTHER INFORMATION: Xaa = X1 being a hydrophobic amino acid, such
      as Phe or Trp
<220> FEATURE:
<221> NAME/KEY: misc_feature
<222> LOCATION: (2)..(2)
<223> OTHER INFORMATION: Xaa = X2 being a hydrophobic amino acid with
      structural similarity to Met, such as Leu or Nle
<220> FEATURE:
<221> NAME/KEY: misc_feature
<222> LOCATION: (4)..(4)
<223> OTHER INFORMATION: Xaa = X3 being an unnatural hydrophobic amino
      acid with structural similarity to Phe, such as 1-naphtylalanine
      (1Nal) and 2-naphtylalanine (2Nal)

<400> SEQUENCE: 3

```
Xaa Xaa Asp Xaa
1
```

<210> SEQ ID NO 4
<211> LENGTH: 8
<212> TYPE: PRT
<213> ORGANISM: Artificial Sequence
<220> FEATURE:
<223> OTHER INFORMATION: amino acid polymer
<220> FEATURE:
<221> NAME/KEY: misc_feature
<222> LOCATION: (1)..(1)
<223> OTHER INFORMATION: Xaa = X4 being Leu or another hydrophobic amino
      acid such as Pro or any proteinogenic charged amino acid, such as
      Arg, Asp, Asn, Lys, His or Glu, preferably in D form
<220> FEATURE:
<221> NAME/KEY: misc_feature
<222> LOCATION: (2)..(2)
<223> OTHER INFORMATION: Xaa = X5 being Ala, beta-Ala, Tyr or Pro
<220> FEATURE:
<221> NAME/KEY: misc_feature
<222> LOCATION: (3)..(3)
<223> OTHER INFORMATION: Xaa = X6 being Tyr, Pro, Phe, Met or a
      hydrophobic amino acid with structural similarity to Met, such as
      Leu or Nle
<220> FEATURE:
<221> NAME/KEY: misc_feature
<222> LOCATION: (4)..(4)
<223> OTHER INFORMATION: Xaa = X7 being Gly, Thr, Ser, Ala, beta-Ala or
      Pro
<220> FEATURE:
<221> NAME/KEY: misc_feature
<222> LOCATION: (5)..(5)
<223> OTHER INFORMATION: Xaa = X1 being a hydrophobic amino acid, such
      as Phe or Trp
<220> FEATURE:
<221> NAME/KEY: misc_feature
<222> LOCATION: (6)..(6)
<223> OTHER INFORMATION: Xaa = X2 being a hydrophobic amino acid with
      structural similarity to Met, such as Leu or Nle
<220> FEATURE:
<221> NAME/KEY: misc_feature
<222> LOCATION: (8)..(8)
<223> OTHER INFORMATION: Xaa = X3 being an unnatural hydrophobic amino
      acid with structural similarity to Phe, such as 1-naphtylalanine
      (1Nal) and 2-naphtylalanine (2Nal)

<400> SEQUENCE: 4

```
Xaa Xaa Xaa Xaa Xaa Xaa Asp Xaa
1               5

<210> SEQ ID NO 5
<211> LENGTH: 4
<212> TYPE: PRT
<213> ORGANISM: Artificial Sequence
<220> FEATURE:
<223> OTHER INFORMATION: amino acid polymer
<220> FEATURE:
<221> NAME/KEY: misc_feature
<222> LOCATION: (1)..(1)
<223> OTHER INFORMATION: Xaa = X4 being Leu or another hydrophobic amino
      acid such as Pro or any proteinogenic charged amino acid, such as
      Arg, Asp, Asn, Lys, His or Glu, preferably in D form
<220> FEATURE:
<221> NAME/KEY: misc_feature
<222> LOCATION: (2)..(2)
<223> OTHER INFORMATION: Xaa = X5 being Ala, beta-Ala, Tyr or Pro
<220> FEATURE:
<221> NAME/KEY: misc_feature
<222> LOCATION: (3)..(3)
<223> OTHER INFORMATION: Xaa = X6 being Tyr, Pro, Phe, Met or a
      hydrophobic amino acid with structural similarity to Met, such as
      Leu or Nle
<220> FEATURE:
<221> NAME/KEY: misc_feature
<222> LOCATION: (4)..(4)
<223> OTHER INFORMATION: Xaa = X7 being Gly, Thr, Ser, Ala, beta-Ala or
      Pro

<400> SEQUENCE: 5

Xaa Xaa Xaa Xaa
1

<210> SEQ ID NO 6
<211> LENGTH: 8
<212> TYPE: PRT
<213> ORGANISM: Artificial Sequence
<220> FEATURE:
<223> OTHER INFORMATION: amino acid polymer
<220> FEATURE:
<221> NAME/KEY: misc_feature
<222> LOCATION: (6)..(6)
<223> OTHER INFORMATION: Xaa being an N-methylated Nle
<220> FEATURE:
<221> NAME/KEY: misc_feature
<222> LOCATION: (8)..(8)
<223> OTHER INFORMATION: Xaa = X3 being an unnatural hydrophobic amino
      acid with structural similarity to Phe, such as 1-naphtylalanine
      (1Nal) and 2-naphtylalanine (2Nal)

<400> SEQUENCE: 6

Pro Ala Tyr Gly Trp Xaa Asp Xaa
1               5

<210> SEQ ID NO 7
<211> LENGTH: 8
<212> TYPE: PRT
<213> ORGANISM: Artificial Sequence
<220> FEATURE:
<223> OTHER INFORMATION: amino acid polymer
<220> FEATURE:
<221> NAME/KEY: misc_feature
<222> LOCATION: (6)..(6)
<223> OTHER INFORMATION: Xaa being an N-methylated Nle
<220> FEATURE:
<221> NAME/KEY: misc_feature
<222> LOCATION: (8)..(8)
<223> OTHER INFORMATION: Xaa = X3 being an unnatural hydrophobic amino
      acid with structural similarity to Phe, such as 1-naphtylalanine
      (1Nal) and 2-naphtylalanine (2Nal)

<400> SEQUENCE: 7
```

```
Leu Ala Tyr Gly Trp Xaa Asp Xaa
1               5

<210> SEQ ID NO 8
<211> LENGTH: 8
<212> TYPE: PRT
<213> ORGANISM: Artificial Sequence
<220> FEATURE:
<223> OTHER INFORMATION: amino acid polymer
<220> FEATURE:
<221> NAME/KEY: misc_feature
<222> LOCATION: (1)..(1)
<223> OTHER INFORMATION: Xaa = X4 being Leu or another hydrophobic amino
      acid such as Pro or any proteinogenic charged amino acid, such as
      Arg, Asp, Asn, Lys, His or Glu, preferably in D form
<220> FEATURE:
<221> NAME/KEY: misc_feature
<222> LOCATION: (6)..(6)
<223> OTHER INFORMATION: Xaa being an N-methylated Nle
<220> FEATURE:
<221> NAME/KEY: misc_feature
<222> LOCATION: (8)..(8)
<223> OTHER INFORMATION: Xaa = X3 being an unnatural hydrophobic amino
      acid with structural similarity to Phe, such as 1-naphtylalanine
      (1Nal) and 2-naphtylalanine (2Nal)

<400> SEQUENCE: 8

Xaa Ala Tyr Gly Trp Xaa Asp Xaa
1               5

<210> SEQ ID NO 9
<211> LENGTH: 8
<212> TYPE: PRT
<213> ORGANISM: Artificial Sequence
<220> FEATURE:
<223> OTHER INFORMATION: amino acid polymer
<220> FEATURE:
<221> NAME/KEY: MISC_FEATURE
<223> OTHER INFORMATION: sequence has DOTA
      (1,4,7,10-tetraazacyclododecan-1,4,7,10-tetraacetic acid) =
      chelator at the N-terminus
<220> FEATURE:
<221> NAME/KEY: MISC_FEATURE
<223> OTHER INFORMATION: amidated at the C-terminus
<220> FEATURE:
<221> NAME/KEY: misc_feature
<222> LOCATION: (1)..(1)
<223> OTHER INFORMATION: Xaa = X4 being Leu or another hydrophobic amino
      acid such as Pro or any proteinogenic charged amino acid, such as
      Arg, Asp, Asn, Lys, His or Glu, preferably in D form
<220> FEATURE:
<221> NAME/KEY: misc_feature
<222> LOCATION: (6)..(6)
<223> OTHER INFORMATION: Xaa being an N-methylated Nle
<220> FEATURE:
<221> NAME/KEY: misc_feature
<222> LOCATION: (8)..(8)
<223> OTHER INFORMATION: Xaa = X3 being an unnatural hydrophobic amino
      acid with structural similarity to Phe, such as 1-naphtylalanine
      (1Nal) and 2-naphtylalanine (2Nal)

<400> SEQUENCE: 9

Xaa Ala Tyr Gly Trp Xaa Asp Xaa
1               5

<210> SEQ ID NO 10
<211> LENGTH: 8
<212> TYPE: PRT
<213> ORGANISM: Artificial Sequence
<220> FEATURE:
<223> OTHER INFORMATION: amino acid polymer
<220> FEATURE:
<221> NAME/KEY: MISC_FEATURE
```

```
<223> OTHER INFORMATION: sequence has DOTA
      (1,4,7,10-tetraazacyclododecan-1,4,7,10-tetraacetic acid) =
      chelator at the N-terminus
<220> FEATURE:
<221> NAME/KEY: MISC_FEATURE
<223> OTHER INFORMATION: amidated at the C-terminus
<220> FEATURE:
<221> NAME/KEY: misc_feature
<222> LOCATION: (1)..(1)
<223> OTHER INFORMATION: Xaa = X4 being Leu or another hydrophobic amino
      acid such as Pro or any proteinogenic charged amino acid, such as
      Arg, Asp, Asn, Lys, His or Glu, preferably in D form
<220> FEATURE:
<221> NAME/KEY: misc_feature
<222> LOCATION: (2)..(2)
<223> OTHER INFORMATION: Xaa = X5 being Ala, beta-Ala, Tyr or Pro
<220> FEATURE:
<221> NAME/KEY: misc_feature
<222> LOCATION: (6)..(6)
<223> OTHER INFORMATION: Xaa being an N-methylated Nle
<220> FEATURE:
<221> NAME/KEY: misc_feature
<222> LOCATION: (8)..(8)
<223> OTHER INFORMATION: Xaa = X3 being an unnatural hydrophobic amino
      acid with structural similarity to Phe, such as 1-naphtylalanine
      (1Nal) and 2-naphtylalanine (2Nal)

<400> SEQUENCE: 10

Xaa Xaa Tyr Gly Trp Xaa Asp Xaa
1               5

<210> SEQ ID NO 11
<211> LENGTH: 8
<212> TYPE: PRT
<213> ORGANISM: Artificial Sequence
<220> FEATURE:
<223> OTHER INFORMATION: amino acid polymer
<220> FEATURE:
<221> NAME/KEY: MISC_FEATURE
<223> OTHER INFORMATION: sequence has DOTA
      (1,4,7,10-tetraazacyclododecan-1,4,7,10-tetraacetic acid) =
      chelator at the N-terminus
<220> FEATURE:
<221> NAME/KEY: MISC_FEATURE
<223> OTHER INFORMATION: amidated at the C-terminus
<220> FEATURE:
<221> NAME/KEY: misc_feature
<222> LOCATION: (1)..(1)
<223> OTHER INFORMATION: Xaa = X4 being Leu or another hydrophobic amino
      acid such as Pro or any proteinogenic charged amino acid, such as
      Arg, Asp, Asn, Lys, His or Glu, preferably in D form
<220> FEATURE:
<221> NAME/KEY: misc_feature
<222> LOCATION: (2)..(2)
<223> OTHER INFORMATION: Xaa = X5 being Ala, beta-Ala, Tyr or Pro
<220> FEATURE:
<221> NAME/KEY: misc_feature
<222> LOCATION: (3)..(3)
<223> OTHER INFORMATION: Xaa = X6 being Tyr, Pro, Phe, Met or a
      hydrophobic amino acid with structural similarity to Met, such as
      Leu or Nle
<220> FEATURE:
<221> NAME/KEY: misc_feature
<222> LOCATION: (6)..(6)
<223> OTHER INFORMATION: Xaa being an N-methylated Nle
<220> FEATURE:
<221> NAME/KEY: misc_feature
<222> LOCATION: (8)..(8)
<223> OTHER INFORMATION: Xaa = X3 being an unnatural hydrophobic amino
      acid with structural similarity to Phe, such as 1-naphtylalanine
      (1Nal) and 2-naphtylalanine (2Nal)

<400> SEQUENCE: 11

Xaa Xaa Xaa Gly Trp Xaa Asp Xaa
1               5
```

```
<210> SEQ ID NO 12
<211> LENGTH: 8
<212> TYPE: PRT
<213> ORGANISM: Artificial Sequence
<220> FEATURE:
<223> OTHER INFORMATION: amino acid polymer
<220> FEATURE:
<221> NAME/KEY: MISC_FEATURE
<223> OTHER INFORMATION: sequence has DOTA
      (1,4,7,10-tetraazacyclododecan-1,4,7,10-tetraacetic acid) =
      chelator at the N-terminus
<220> FEATURE:
<221> NAME/KEY: MISC_FEATURE
<223> OTHER INFORMATION: amidated at the C-terminus
<220> FEATURE:
<221> NAME/KEY: misc_feature
<222> LOCATION: (1)..(1)
<223> OTHER INFORMATION: Xaa = X4 being Leu or another hydrophobic amino
      acid such as Pro or any proteinogenic charged amino acid, such as
      Arg, Asp, Asn, Lys, His or Glu, preferably in D form
<220> FEATURE:
<221> NAME/KEY: misc_feature
<222> LOCATION: (2)..(2)
<223> OTHER INFORMATION: Xaa = X5 being Ala, beta-Ala, Tyr or Pro
<220> FEATURE:
<221> NAME/KEY: misc_feature
<222> LOCATION: (3)..(3)
<223> OTHER INFORMATION: Xaa = X6 being Tyr, Pro, Phe, Met or a
      hydrophobic amino acid with structural similarity to Met, such as
      Leu or Nle
<220> FEATURE:
<221> NAME/KEY: misc_feature
<222> LOCATION: (4)..(4)
<223> OTHER INFORMATION: Xaa = X7= Gly, Thr, Ser, Ala, beta-Ala or Pro
<220> FEATURE:
<221> NAME/KEY: misc_feature
<222> LOCATION: (6)..(6)
<223> OTHER INFORMATION: Xaa being an N-methylated Nle
<220> FEATURE:
<221> NAME/KEY: misc_feature
<222> LOCATION: (8)..(8)
<223> OTHER INFORMATION: Xaa = X3 being an unnatural hydrophobic amino
      acid with structural similarity to Phe, such as 1-naphtylalanine
      (1Nal) and 2-naphtylalanine (2Nal)

<400> SEQUENCE: 12

Xaa Xaa Xaa Xaa Trp Xaa Asp Xaa
1               5

<210> SEQ ID NO 13
<211> LENGTH: 8
<212> TYPE: PRT
<213> ORGANISM: Artificial Sequence
<220> FEATURE:
<223> OTHER INFORMATION: amino acid polymer
<220> FEATURE:
<221> NAME/KEY: MISC_FEATURE
<223> OTHER INFORMATION: sequence has DOTA
      (1,4,7,10-tetraazacyclododecan-1,4,7,10-tetraacetic acid) =
      chelator at the N-terminus
<220> FEATURE:
<221> NAME/KEY: MISC_FEATURE
<223> OTHER INFORMATION: amidated at the C-terminus
<220> FEATURE:
<221> NAME/KEY: misc_feature
<222> LOCATION: (1)..(1)
<223> OTHER INFORMATION: Xaa = X4 being Leu or another hydrophobic amino
      acid such as Pro or any proteinogenic charged amino acid, such as
      Arg, Asp, Asn, Lys, His or Glu, preferably in D form
<220> FEATURE:
<221> NAME/KEY: misc_feature
<222> LOCATION: (2)..(2)
<223> OTHER INFORMATION: Xaa = X5 being Ala, beta-Ala, Tyr or Pro
<220> FEATURE:
<221> NAME/KEY: misc_feature
<222> LOCATION: (3)..(3)
```

```
<223> OTHER INFORMATION: Xaa = X6 being Tyr, Pro, Phe, Met or a
      hydrophobic amino acid with structural similarity to Met, such as
      Leu or Nle
<220> FEATURE:
<221> NAME/KEY: misc_feature
<222> LOCATION: (4)..(4)
<223> OTHER INFORMATION: Xaa = X7= Gly, Thr, Ser, Ala, beta-Ala or Pro
<220> FEATURE:
<221> NAME/KEY: misc_feature
<222> LOCATION: (5)..(5)
<223> OTHER INFORMATION: Trp being N-methylated
<220> FEATURE:
<221> NAME/KEY: misc_feature
<222> LOCATION: (6)..(6)
<223> OTHER INFORMATION: Xaa being an N-methylated Nle
<220> FEATURE:
<221> NAME/KEY: misc_feature
<222> LOCATION: (8)..(8)
<223> OTHER INFORMATION: Xaa = X3 being an unnatural hydrophobic amino
      acid with structural similarity to Phe, such as 1-naphtylalanine
      (1Nal) and 2-naphtylalanine (2Nal)

<400> SEQUENCE: 13

Xaa Xaa Xaa Xaa Trp Xaa Asp Xaa
1               5

<210> SEQ ID NO 14
<211> LENGTH: 8
<212> TYPE: PRT
<213> ORGANISM: Artificial Sequence
<220> FEATURE:
<223> OTHER INFORMATION: amino acid polymer
<220> FEATURE:
<221> NAME/KEY: MISC_FEATURE
<223> OTHER INFORMATION: sequence has DOTA
      (1,4,7,10-tetraazacyclododecan-1,4,7,10-tetraacetic acid) =
      chelator at the N-terminus
<220> FEATURE:
<221> NAME/KEY: MISC_FEATURE
<223> OTHER INFORMATION: amidated at the C-terminus
<220> FEATURE:
<221> NAME/KEY: misc_feature
<222> LOCATION: (1)..(1)
<223> OTHER INFORMATION: Xaa = X4 being Leu or another hydrophobic amino
      acid such as Pro or any proteinogenic charged amino acid, such as
      Arg, Asp, Asn, Lys, His or Glu, preferably in D form
<220> FEATURE:
<221> NAME/KEY: misc_feature
<222> LOCATION: (2)..(2)
<223> OTHER INFORMATION: Xaa = X5 being Ala, beta-Ala, Tyr or Pro
<220> FEATURE:
<221> NAME/KEY: misc_feature
<222> LOCATION: (3)..(3)
<223> OTHER INFORMATION: Xaa = X6 being Tyr, Pro, Phe, Met or a
      hydrophobic amino acid with structural similarity to Met, such as
      Leu or Nle
<220> FEATURE:
<221> NAME/KEY: misc_feature
<222> LOCATION: (4)..(4)
<223> OTHER INFORMATION: Gly being N-methylated
<220> FEATURE:
<221> NAME/KEY: misc_feature
<222> LOCATION: (6)..(6)
<223> OTHER INFORMATION: Xaa being an N-methylated Nle
<220> FEATURE:
<221> NAME/KEY: misc_feature
<222> LOCATION: (8)..(8)
<223> OTHER INFORMATION: Xaa = X3 being an unnatural hydrophobic amino
      acid with structural similarity to Phe, such as 1-naphtylalanine
      (1Nal) and 2-naphtylalanine (2Nal)

<400> SEQUENCE: 14

Xaa Xaa Xaa Gly Trp Xaa Asp Xaa
1               5
```

```
<210> SEQ ID NO 15
<211> LENGTH: 8
<212> TYPE: PRT
<213> ORGANISM: Artificial Sequence
<220> FEATURE:
<223> OTHER INFORMATION: amino acid polymer
<220> FEATURE:
<221> NAME/KEY: MISC_FEATURE
<223> OTHER INFORMATION: sequence has DOTA
      (1,4,7,10-tetraazacyclododecan-1,4,7,10-tetraacetic acid) =
      chelator at the N-terminus
<220> FEATURE:
<221> NAME/KEY: MISC_FEATURE
<223> OTHER INFORMATION: amidated at the C-terminus
<220> FEATURE:
<221> NAME/KEY: misc_feature
<222> LOCATION: (1)..(1)
<223> OTHER INFORMATION: Xaa = X4 being Leu or another hydrophobic amino
      acid such as Pro or any proteinogenic charged amino acid, such as
      Arg, Asp, Asn, Lys, His or Glu, preferably in D form
<220> FEATURE:
<221> NAME/KEY: misc_feature
<222> LOCATION: (2)..(2)
<223> OTHER INFORMATION: X5 being N-methylated
<220> FEATURE:
<221> NAME/KEY: misc_feature
<222> LOCATION: (2)..(2)
<223> OTHER INFORMATION: Xaa = X5 being Ala, beta-Ala, Tyr or Pro
<220> FEATURE:
<221> NAME/KEY: misc_feature
<222> LOCATION: (3)..(3)
<223> OTHER INFORMATION: Xaa = X6 being Tyr, Pro, Phe, Met or a
      hydrophobic amino acid with structural similarity to Met, such as
      Leu or Nle
<220> FEATURE:
<221> NAME/KEY: misc_feature
<222> LOCATION: (6)..(6)
<223> OTHER INFORMATION: Xaa being an N-methylated Nle
<220> FEATURE:
<221> NAME/KEY: misc_feature
<222> LOCATION: (8)..(8)
<223> OTHER INFORMATION: Xaa = X3 being an unnatural hydrophobic amino
      acid with structural similarity to Phe, such as 1-naphtylalanine
      (1Nal) and 2-naphtylalanine (2Nal)

<400> SEQUENCE: 15

Xaa Xaa Xaa Gly Trp Xaa Asp Xaa
1               5

<210> SEQ ID NO 16
<211> LENGTH: 8
<212> TYPE: PRT
<213> ORGANISM: Artificial Sequence
<220> FEATURE:
<223> OTHER INFORMATION: amino acid polymer
<220> FEATURE:
<221> NAME/KEY: MISC_FEATURE
<223> OTHER INFORMATION: sequence has DOTA
      (1,4,7,10-tetraazacyclododecan-1,4,7,10-tetraacetic acid) =
      chelator at the N-terminus
<220> FEATURE:
<221> NAME/KEY: MISC_FEATURE
<223> OTHER INFORMATION: amidated at the C-terminus
<220> FEATURE:
<221> NAME/KEY: misc_feature
<222> LOCATION: (1)..(1)
<223> OTHER INFORMATION: X4 being N-methylated
<220> FEATURE:
<221> NAME/KEY: misc_feature
<222> LOCATION: (1)..(1)
<223> OTHER INFORMATION: Xaa = X4 being Leu or another hydrophobic amino
      acid such as Pro or any proteinogenic charged amino acid, such as
      Arg, Asp, Asn, Lys, His or Glu, preferably in D form
<220> FEATURE:
<221> NAME/KEY: misc_feature
<222> LOCATION: (2)..(2)
<223> OTHER INFORMATION: Xaa = X5 being Ala, beta-Ala, Tyr or Pro
```

```
<220> FEATURE:
<221> NAME/KEY: misc_feature
<222> LOCATION: (3)..(3)
<223> OTHER INFORMATION: Xaa = X6 being Tyr, Pro, Phe, Met or a
      hydrophobic amino acid with structural similarity to Met, such as
      Leu or Nle
<220> FEATURE:
<221> NAME/KEY: misc_feature
<222> LOCATION: (6)..(6)
<223> OTHER INFORMATION: Xaa being an N-methylated Nle
<220> FEATURE:
<221> NAME/KEY: misc_feature
<222> LOCATION: (8)..(8)
<223> OTHER INFORMATION: Xaa = X3 being an unnatural hydrophobic amino
      acid with structural similarity to Phe, such as 1-naphtylalanine
      (1Nal) and 2-naphtylalanine (2Nal)

<400> SEQUENCE: 16

Xaa Xaa Xaa Gly Trp Xaa Asp Xaa
1               5

<210> SEQ ID NO 17
<211> LENGTH: 10
<212> TYPE: PRT
<213> ORGANISM: Artificial Sequence
<220> FEATURE:
<223> OTHER INFORMATION: radiolabelled MG analogue
<220> FEATURE:
<221> NAME/KEY: MISC_FEATURE
<223> OTHER INFORMATION: sequence has DOTA
      (1,4,7,10-tetraazacyclododecan-1,4,7,10-tetraacetic acid) =
      chelator at the N-terminus
<220> FEATURE:
<221> NAME/KEY: MISC_FEATURE
<223> OTHER INFORMATION: amidated at the C-terminus

<400> SEQUENCE: 17

His His Glu Ala Tyr Gly Trp Met Asp Phe
1               5                   10

<210> SEQ ID NO 18
<211> LENGTH: 5
<212> TYPE: PRT
<213> ORGANISM: Artificial Sequence
<220> FEATURE:
<223> OTHER INFORMATION: pentagastrin
<220> FEATURE:
<221> NAME/KEY: MISC_FEATURE
<223> OTHER INFORMATION: sequence has Boc (tert-butyloxycarbonyl group)
      at the N-terminus
<220> FEATURE:
<221> NAME/KEY: MISC_FEATURE
<223> OTHER INFORMATION: amidated at the C-terminus
<220> FEATURE:
<221> NAME/KEY: misc_feature
<222> LOCATION: (1)..(1)
<223> OTHER INFORMATION: Xaa = beta-Ala

<400> SEQUENCE: 18

Xaa Trp Met Asp Phe
1               5
```

PHARMACOKINETICS AND CHOLECYSTOKININ-2 RECEPTOR (CCK2R) TARGETING FOR DIAGNOSIS AND THERAPY

STATEMENT OF PRIORITY

This application is a 35 U.S.C. § 371 national phase application of PCT Application PCT/EP2018/065206, filed Jun. 8, 2018, which claims priority to European Patent Application No. 17174973.2, filed Jun. 8, 2017, the entire contents of each of which are incorporated by reference herein in its entirety.

STATEMENT REGARDING ELECTRONIC FILING OF A SEQUENCE LISTING

A Sequence Listing in ASCII text format, submitted under 37 C.F.R. § 1.821, entitled 1549-2_ST25.txt, 16,056 bytes in size, generated on Dec. 6, 2019 and filed via EFS-Web, is provided in lieu of a paper copy. This Sequence Listing is incorporated by reference into the specification for its disclosures.

BACKGROUND OF THE INVENTION

The invention among other things relates to a peptidomimetic with improved properties for specific cholecystokinin-2 receptor (CCK2R) targeting and its diagnostic and therapeutic use. Cholecystokinin receptors are classified into two receptors subtypes, CCK1R and CCK2R. CCK2R have been identified in various tumours such as neuroendocrine tumours, medullary thyroid carcinomas (MTC), small cell lung cancers (SCLC), leiomyosarcomas/leiomyomas, gastrointestinal stromal tumours, insulinomas, vipomas, carcinoids, astrocytomas, stromal ovarian cancers, breast and endometrial adenocarcinomas, and others (Reubi J C et al., Cancer Res 1997, 57: 1377-1386; Reubi J C, Curr Top Med Chem 2007, 7: 1239-1242; Sanchez C et al. Mol Cell Endocrinol 2012, 349: 170-179), while CCK1R are expressed only in a limited number of human tumours. Different radiolabelled peptide probes have been developed based on the endogenous ligands for CCK2R, cholecystokinin (CCK) or gastrin. The two peptides CCK and gastrin bind to CCK2R with almost the same affinity and potency and share a common bioactive region at the C-terminus, Trp-Met-Asp-Phe (Dufresne M et al., Physiol Rev 2006, 86: 805-847), which proved to be essential for receptor binding (Tracy H J et al., Nature 1964, 204: 935-938). Due to the very short physiological half-life of the parent peptide, additional synthetic modifications of the peptide are generally required to metabolically stabilize the linear amino acid sequence for medical applications (Fani M et al., Theranostics 2012, 2: 481-501). Such modifications have been explored also for radiolabelled CCK and gastrin analogues (Roosenburg S et al., Amino Acids 2011, 41: 1049-1058). Beside radioligands based on Asp-Tyr-Met-Gly-Trp-Met-Asp-Phe-$NH_2$ (CCK8; SEQ ID NO:1) and Leu-Glu-Glu-Glu-Glu-Glu-Ala-Tyr-Gly-Trp-Met-Asp-Phe-$NH_2$ (minigastrin, MG; SEQ ID NO:2), also nonpeptidic ligands have been proposed (Wayua C et al., J Nucl Med 2015, 56: 113-119). CCK2R specific tumour uptake could be recently proven also in nude mice bearing tumour xenografts derived from colorectal adenocarcinoma cells by optical imaging with a fluorescent CCK2R-targeted MG analogue (dQ-MG-754) (Kossatz S et al., Biomaterials 2013, 34: 5172-5180). By using the potent CCK2R ligand Z-360 conjugated to tubulysin B delivering the cytotoxic drug selectively to CCK2R-positive tumours tumour regression could be observed in a preclinical animal model (Wayua C et al., Mol Pharm 2015, 12: 2477-2483).

Using radiolabelled [diethylenetriaminepentaacetic$^0$,D-Glu$^1$]minigastrin (DTPA-MG0) good tumour targeting properties have been obtained, however also a very high kidney uptake was observed leading to severe renal side effects in patients treated with $^{90}$Y-labelled DTPA-MG0 (Béhé Metal., Biopolymers 2002, 66: 399-418). $^{111}$In-DTPA-MG0 has however proven to be superior to somatostatin receptor scintigraphy and 2-deoxy-2-[$^{18}$F]fluoro-D-glucose positron emission tomography (FDG PET) for tumour detection in patients with MTC and SCLC and has shown to be of additional value also in neuroendocrine tumours with low somatostatin receptor expression (Gotthardt M et al., Eur J Nucl Med Mol Imaging 2006, 33: 1273-1279; Gotthardt M et al., Endocr Relat Cancer 2006, 13: 1203-1211).

With the truncated $^{111}$In-labelled peptide analogue, [1,4,7,10-tetraazacyclodocecan-1,4,7,10-tetraacetic acid$^0$,D-Glu$^1$,DesGlu$^{2-6}$]minigastrin (DOTA-MG11) a significantly reduced kidney uptake was shown in animal studies (Behe M et al., Eur J Nucl Med Mol Imaging 2005: 32, S78) and confirmed in a first clinical study (Fröberg A C et al., Eur J Nucl Med Mol Imaging 2009, 36: 1265-1272). However, due to a clearly reduced stability against enzymatic degradation and low biological half-life below five minutes in vivo (Breeman W A et al., Nucl Med Biol 2008, 35: 839-849) only a poor diagnostic efficacy was observed with $^{111}$In-DOTA-MG11. To increase enzymatic stability and improve specific receptor targeting while reducing kidney retention different modifications in the peptide sequence have been attempted in the N-terminal region of the peptide (Aloj L et al., Eur J Nucl Med Mol Imaging 2011, 38: 1417-1425; Laverman P et al., Eur J Nucl Med Mol Imaging 2011, 38: 1410-1416). Only very view modifications have been attempted also in the C-terminal region and are limited to substitution of methionine with unnatural amino acids such as norleucine or homopropargylglycin to prevent methionine oxidation associated with loss of receptor affinity (Mather S J et al., J Nucl Med 2007, 48: 615-622; Roosenburg S et al., Bioconjug Chem 2010, 21: 663-670). However, the analysis of blood and urine of BALB/c mice injected with these different new peptide analogues labelled with $^{177}$Lu, has shown, that already 10 min after injection no intact radioligand could be detected (Ocak M et al., Eur J Nucl Med Mol Imaging 2011, 38: 1426-1435). Also the non-canonical amino acid methoxinine has been recently used to substitute the oxidation sensitive methionine residue and chemically stabilize MG analogues (Grob N M et al., J Pept Sci 2017, 23: 38-44), without improving however the biological half-life. The above mentioned studies make clear that the chemical modifications adopted so far are not successful in improving the biological half-life and targeting properties in vivo.

The present inventors have previously generated two $^{111}$In-labelled peptide analogues with the structures $^{111}$In-DOTA-DGlu-Ala-Tyr-Gly-Trp-Met-Asp-1Nal-$NH_2$ and $^{111}$In-DOTA-DGlu-Ala-Tyr-Gly-Trp-(N-Me)Nle-Asp-(N-Me)Phe-$NH_2$, referred to as MGS1 and MGS4, respectively (Klingler Metal., Eur J Nucl Med Mol Imaging 2017, 44: S228). These peptide analogues showed increased stability in serum compared to DOTA-MG11. However, further improvements with regard to cellular uptake and specific receptor targeting were desired. Therefore, the present inventors developed further peptidomimetics and investigated their enzymatic stability, receptor affinity and specific receptor targeting, including cellular uptake in vitro and tumour uptake in vivo evaluating also the kidney retention. The present inventors surprisingly found that a new group of peptidomimetics that target CCK2R possesses superior stability against enzymatic degradation while at the same time having improved tumour uptake and retention in vivo. Without being bound by any particular theory, it is currently believed that the improved tumor uptake and retention is at least in part due to an improved cellular uptake.

SUMMARY OF THE INVENTION

It is an objective of the present invention to improve the half-life in serum, preferably also the in vivo stability, cellular uptake, and tumour targeting properties, while retaining low kidney retention, of CCK2R targeting peptidomimetics. This objective is achieved according to the present invention by the following embodiments and aspects of the invention.

In a first embodiment, the present invention provides a peptidomimetic comprising an amino acid polymer with the sequence $X^1$-$X^2$-Asp-$X^3$ (SEQ ID NO:3), wherein $X^1$ is a hydrophobic amino acid, such as Phe or Trp, $X^2$ is a hydrophobic amino acid with structural similarity to Met, such as Leu or Nle, $X^3$ is an unnatural hydrophobic amino acid with structural similarity to Phe, such as 1Nal and 2Nal, and the peptidomimetic has a length of 5 to 50 amino acids.

In preferred embodiments, the peptidomimetic of the present invention comprises an amino acid polymer with the sequence $X^4$-$X^5$-$X^6$-$X^7$-$X^1$-$X^2$-Asp-$X^3$ (SEQ ID NO:4), wherein $X^4$ is Leu or another hydrophobic amino acid such as Pro or any proteinogenic charged amino acid, such as Arg, Asp, Lys, His or Glu, preferably in D form, $X^5$ is Ala, beta-Ala, Tyr or Pro, $X^6$ is Tyr, Pro, Phe, Met or a hydrophobic amino acid with structural similarity to Met, such as Leu or Nle, and $X^7$ is Gly, Thr, Ser, Ala, beta-Ala or Pro. In further embodiments, at least one of the bonds (—) between a chemical group conjugated to the N-terminus and $X^4$, $X^4$ and $X^5$, $X^5$ and $X^6$, $X^6$ and $X^7$, $X^7$ and $X^1$, $X^1$ and $X^2$, $X^2$ and Asp, and Asp and $X^3$ is an isopeptide bond or a pseudopeptide bond, such as —NHCO—, —CONCH$_3$— or —CH$_2$NH—. Preferably, the C-terminus is amidated. Preferably, the peptidomimetic comprises 8 to 13 amino acids. In some embodiments the peptidomimetic comprises a reporter group or a cytotoxic group. In some embodiments, the reporter group or cytotoxic group is coordinated by a chelator that is comprised by the peptidomimetic. In some embodiments, the reporter group or cytotoxic group is part of a prosthetic group that is comprised by the peptidomimetic. Preferably, the reporter group or cytotoxic group is a radionuclide.

In another embodiment the present invention provides a method of producing the peptidomimetic of the present invention comprising synthesizing the amino acid polymer.

Further, the present invention provides a pharmaceutical or diagnostic composition comprising the peptidomimetic of the present invention.

The present invention also provides a use of the peptidomimetic of the present invention for delivering a reporter group or a cytotoxic group to a cell.

In another aspect, the present invention provides a method of targeting and imaging cells, wherein the method comprises the steps of a) contacting a cell with the peptidomimetic of the present invention, wherein the peptidomimetic comprises a reporter group, and b) visualizing the reporter group that is in contact with the cell.

In a preferred embodiment, the contacting comprises administering the peptidomimetic of the present invention, wherein the peptidomimetic comprises a reporter group, to a patient, preferably wherein the patient has cancer.

The present invention also provides the peptidomimetic of the present invention for use in therapy.

The present invention also provides the peptidomimetic of the present invention for use in the treatment of cancer, preferably the cancer is a cancer that expresses CCK2R on the surface of tumour cells.

The present invention further provides the peptidomimetic of the present invention for use in diagnosis, preferably the diagnosis of cancer, more preferably the types of cancer mentioned herein.

In preferred embodiments the peptidomimetics of the present invention specifically bind to CCK2R. Specific binding to CCK2R allows targeting of cells and tissue that express CCK2R over cells and tissue that does not express CCK2R. This characteristic of the peptidomimetics of the present invention is useful for diagnostic and therapeutic purposes, for example, for the diagnosis and treatment of certain types of cancer, in particular cancers that express CCK2R. The teaching of the present invention is, however, not limited to cancer, but pertains to any disease that is associated with the expression of CCK2R. In particular, the peptidomimetics of the present invention are useful for diagnostic and therapeutic purposes, since they show a high level of cellular uptake (cellular internalization) by cells that express CCK2R. Further, the peptidomimetics of the present invention are useful, since they are particularly stable against degradation, in particular degradation in serum by proteases, preferably metabolic degradation in vivo by a variety of proteolytic enzymes. Moreover, the peptidomimetics of the present invention are useful, since they do not accumulate in the kidneys, or they only accumulate in the kidneys to a low level that is not harmful to the patient that is treated with the peptidomimetic of the present invention.

The above embodiments are particularly preferred embodiments of the present invention. It is emphasized that any combination of the above embodiments, or respective technical features therein, is also disclosed herein as part of the present invention. The skilled person understands that the present invention is not limited to the embodiments explicitly recited above, but also includes combinations not explicitly disclosed above or below. Such combinations result, for example, from combining aspects, embodiments or features of the present invention mentioned above with aspects, embodiments or features of the present invention disclosed below in the detailed description of the present invention. The skilled person will appreciate that, in fact, the above described embodiments are to be considered together with the corresponding sections of the detailed description given further below, as well as with the examples set out in this application. Further, any headings given in the description are not generally to be construed as being limiting on the subject matter disclosed under the heading, that is, the subject matter disclosed under one heading can be read in combination with the subject matter described under a different heading.

Other aspects, embodiments, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from the detailed description.

BRIEF DESCRIPTION OF DRAWINGS

The invention will be described in more detail in the following section and illustrated in accompanying figures showing in.

DETAILED DESCRIPTION OF THE INVENTION

Figure 1:
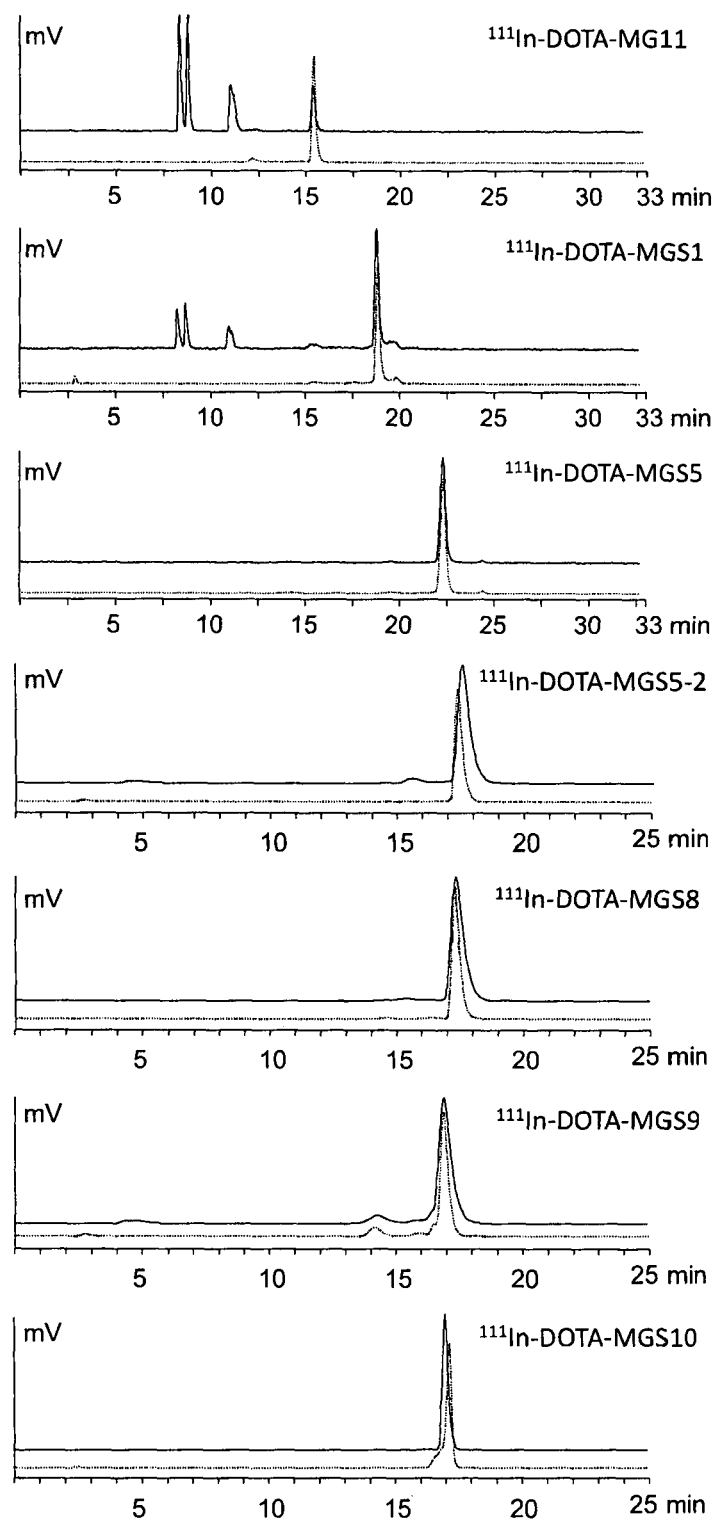
FIG. 1 the stability against enzymatic degradation in human serum in comparison with $^{111}$In-DOTA-MG11 and $^{111}$In-DOTA-MGS1 as analyzed by radio-HPLC after incubation of the $^{111}$In-labelled peptidomimetics of the present invention in human serum for 24 h: radiochemical purity after radiolabelling (dotted line), radio-HPLC after incubation in human serum (solid line).
Figure 1:
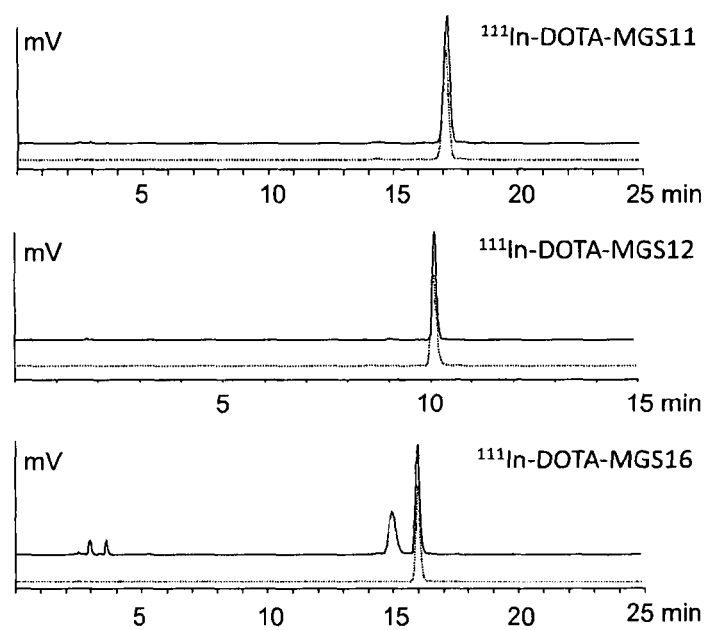

All publications, including but not limited to patents, patent applications and scientific publications, cited in this description are herein incorporated by reference for all purposes as if each individual publication were specifically and individually indicated to be incorporated by reference.

The use of the term "comprising" as well as other grammatical forms such as "comprises" and "comprised" is not limiting. The terms "comprising", "comprises" and "comprised" should be understood as referring to an open-ended description of an embodiment of the present invention that may, but does not have to, include additional technical features in addition to the explicitly stated technical features. In the same sense the term "involving" as well as other respective grammatical forms such as "involves" and "involved" is not limiting. The same applies for the term "including" and other grammatical forms such as "includes" and "included". Section headings throughout the description are for organizational purposes only. In particular, they are not intended as limiting for various embodiments described therein, and it is to be understood that embodiments (and features therein) described under one subheading may be freely combined with embodiments (and features therein) described under another subheading. Further, the terms "comprising", "involving" and "including", and any grammatical forms thereof, are not to be interpreted to exclusively refer to embodiments that include additional features to those explicitly recited. These terms equally refer to embodiments that consist of only those features that are explicitly mentioned.

As used herein, the term "peptidomimetic", "peptide analogue" or "peptide derivative" or "peptide conjugate" refers to a compound that comprises a polymer of two or more amino acids that comprises at least one unnatural amino acid, pseudopeptide bond or chemical moiety that is different from an amino acid, such as a reporter group or a cytotoxic group, including also a chelator, a prosthetic group, a linker or a pharmacokinetic modifier. A peptidomimetic as defined herein generally mimics a biological activity of a natural peptide. In the present case the peptidomimetics of the present invention mimic the ability, in the sense of having the ability, of the natural CCK2R ligands, such as gastrin, to bind to CCK2R.

As used herein, the term "amino acid polymer" refers to a polymer of two or more amino acids.

The term "peptide" refers to a polymer of two or more proteinogenic amino acids in L-form that are connected by amide bonds.

The term "amino acid" as used herein refers to a compound that contains in its monomeric state at least an amine (—NH$_2$) and a carboxyl (—COOH) functional group. If bonded to another amino acid through a peptide bond, the amine or carboxyl group of the amino acid will from an amide group —CONH— with an amine or carboxyl group of the other amino acid. If an amino acid is conjugated to another amino acid through a pseudopeptide bond, as described below, the amine or carboxyl group may be replaced by other chemical moieties depending on the nature of the pseudopeptide bond. Preferably, the term "amino acid" as used herein refers to alpha- or beta-amino acids. As used herein the term "amino acid" includes the proteinogenic amino acids alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); valine (Val) and selenocysteine (Sec). The term "amino acid" as used herein also includes unnatural amino acids.

"Unnatural amino acids" in the sense of the present application are non-proteinogenic amino acids that occur naturally or are chemically synthesized, for example, norleucine (Nle), methoxinine, homopropargylglycin, ornithine, norvaline, homoserine, and other amino acid analogues such as those described in Liu C C, Schultz P G, Annu Rev Biochem 2010, 79: 413-444 and Liu D R, Schultz P G, Proc Natl Acad Sci USA 1999, 96: 4780-4785. An unnatural amino acid, as used herein, may be, for instance, a proteinogenic amino acid in D-form, for instance, DGlu. Additional contemplated unnatural amino acids are para-, ortho- or meta-substituted phenylalanine, such as para-ethynylphenylalanine, 4-Cl-phenylalanine (Cpa), 4-amino-phenylalanine, and 4-NO$_2$-phenylalanine, homoprolin, homoalanine, beta-alanine, 1-naphthylalanine (1Nal), 2-naphtylalanine (2Nal), p-benzoyl-phenylalanine (Bpa), biphenylalanine (Bip), homophenylalanine (hPhe), homopropargylglycine (Hpg), azidohomoalanine (Aha), cyclohexylalanine (Cha), aminohexanoic acid (Ahx), 2-aminobutanoic acid (Abu), azidonorleucine (Ani), tert-leucine (Tle), 4-amino-carbamoyl-phenylalanine (Aph(Cbm)), 4-amino-hydroorotyl-phenylalanine (Aph(Hor)), S-Acetamidomethyl-L-cysteine (Cys(Acm)), 3-benzothienylalanine, 4-amino-3-hydroxy-6-methylheptanoic acid (Sta). Some of these unnatural amino acids have been explored already for somatostatin and bombesin analogues (Fani M et al., J Nucl Med 2011, 52: 1110-1118; Ginj Metal., Proc Natl Acad Sci USA 2006, 103: 16436-16441; Ginj Metal., Clin Cancer Res 2005, 11: 1136-1145; Mansi R, J Med Chem 2015, 58: 682-691).

As used herein, the term "hydrophobic amino acid" refers to amino acids that have a net zero charge at physiological pH (about pH 7.4). Hydrophobic amino acids can be proteinogenic hydrophobic amino acids or unnatural hydrophobic amino acids. Proteinogenic hydrophobic amino acids are for example serine, threonine, cysteine, selenocysteine, glycine, proline, alanine, valine, isoleucine, leucine, methionine, phenylalanine, tyrosine or tryptophan. Preferred proteinogenic hydrophobic amino acids are proline, isoleucine, leucine, phenylalanine, tyrosine and tryptophan. Unnatural hydrophobic amino acids are, for example, norleucine (Nle), methoxinine, tert-leucine (Tle), 1-naphthylalanine (1Nal), 2-naphtylalanine (2Nal), 3-benzothienylalanine, p-benzoyl-phenylalanine (Bpa), biphenylalanine (Bip), homophenylalanine (hPhe), homopropargylglycine (Hpg), azidohomoalanine (Aha), cyclohexylalanine (Cha), aminohexanoic acid (Ahx), 2-aminobutanoic acid (Abu), azidonorleucine (Anl), 2-aminooctynoic acid (Aoa), norvaline (Nva), para-ethynylphenylalanine, 4-Cl-phenylalanine, homoproline and homoalanine.

A "hydrophobic amino acid with structural similarity to Met" as used herein is a hydrophobic amino acid as defined above that has a similar molecular geometry as and/or is a bioisostere of Met. In particular, in the context of the present invention, an unnatural hydrophobic amino acid with structural similarity to Met can be inserted at position $X^2$ and/or position $X^6$ while maintaining sufficient cellular uptake of the peptidomimetic. Sufficient cellular uptake of the peptidomimetic is maintained, if the cellular uptake of the peptidomimetic is at least about 10%, about 20%, about 30%, about 40%, about 50%, about 60%, about 70%, about 80%, about 90%, or about 95% of the total activity in an assay as described in Example 5. A "hydrophobic amino acid with structural similarity to Met" as used herein may be a proteinogenic hydrophobic amino acid or an unnatural hydrophobic amino acid, preferably Nle or Leu.

An "unnatural hydrophobic amino acid with structural similarity to Phe" as used herein is an unnatural hydrophobic amino acid as defined above that has a similar molecular geometry as and/or is a bioisostere of Phe. In particular, in the context of the present invention, an unnatural hydrophobic amino acid with structural similarity to Phe can be inserted at position $X^3$ while maintaining sufficient cellular uptake of the peptidomimetic. Sufficient cellular uptake of the peptidomimetic is maintained, if the cellular uptake of the peptidomimetic is at least about 10%, about 20%, about 30%, about 40%, about 50%, about 60%, about 70%, about 80%, about 90%, or about 95% of the total activity in an assay as described in Example 5. Preferably, an "unnatural hydrophobic amino acid with structural similarity to Phe" as used herein is 1Nal or 2Nal.

In some embodiments the peptidomimetics of the present invention have a cellular uptake (i.e. binding to the cell membrane and internalization into the cells) to a degree of at least about 10%, about 20%, about 30%, about 40%, about 50%, about 60%, about 70%, about 80%, about 90%, or about 95% of the total activity in an assay as described in Example 5.

In some embodiments the peptidomimetics of the present invention specifically bind to CCK2R. The binding affinity of the peptidomimetics of the invention can be at least about 2%, about 10%, about 20%, about 30%, about 40%, about 50%, about 60%, about 70%, about 80%, about 90%, about 95%, or about 100% of the binding affinity of CCK8, minigastrin or pentagastrin for CCK2R. In some embodiments of the present invention the binding affinity of the peptidomimetics can even be higher than the binding affinity of CCK8, minigastrin or pentagastrin for CCK2R, for example, at least about 110%, about 120%, about 130%, about 140%, about 150%, about 160%, about 170%, about 180%, about 190%, about 200%, about 500%, about 1000%, about 1500%, or about 2000% of the binding affinity of CCK8, minigastrin or pentagastrin for CCK2R in an assay as described in Example 4. Specific binding to CCK2R in the context of the present invention means binding of the peptidomimetic of the present invention to CCK2R that can be displaced with a cognate ligand of CCK2R, such as gastrin, or a radiolabelled variant of a cognate ligand, such as [$^{125}$I]Tyr$^{12}$-labelled gastrin-I. The half maximal inhibitory concentration (IC50) is a measure of this specific binding as explained above and can be obtained from an assay as described in Example 4.

Binding affinity according to the present invention is determined by measuring the half maximal inhibitory concentration (IC50), wherein binding affinity and IC50 value have an inverse relationship, meaning that binding affinity increases with decreasing IC50 value and binding affinity decreases with increasing IC50 value. Therefore, a binding affinity of about 50% means that the IC50 value is about twice as high as the IC50 value of CCK8, minigastrin or pentagastrin for CCK2R.

The term "charged amino acid" as used herein includes amino acids that have non-zero net charge at a physiological pH of about 7.4 and includes proteinogenic and unnatural amino acids, for instance, the proteinogenic amino acids Arg, Lys, His, Glu, and Asp.

The structure of the peptidomimetic is indicated in the three letter amino acid code known to the person skilled in the art, starting with the N-terminus (amino terminus) of the peptidomimetic on the left and ending with the C-terminus of the peptidomimetic on the right. For example, the tetra peptidomimetic or peptide "$X^4$-$X^5$-$X^6$-$X^7$" (SEQ ID NO:5), consisting of four amino acids $X^4$, $X^5$, $X^6$ and $X^7$, has amino acid $X^4$ at the N-terminus and amino acid $X^7$ at the C-terminus. A hyphen, "-", indicates a chemical bond between two individual amino acids, for instance, $X^4$ and $X^5$.

The chemical bond that connects two amino acids of the peptidomimetic of the present invention may be a peptide bond, i.e., an amide bond (—CONH—). A peptide bond as used herein can be formed between an amino group attached to the alpha carbon of one amino acid and the carboxyl group attached to the alpha carbon of another amino acid. A peptide bond may also form between an amino group and a carboxyl group, one of which is not attached to the alpha carbon of the amino acid, but to the side chain of the amino acid (isopeptide bond), for example the amino group in the side chain of lysine. The chemical bond may also be a pseudopeptide bond. In preferred embodiments, the chemical bond that connects two amino acids of the peptidomimetic is an amide bond.

The term "pseudopeptide bond" as used herein refers to a bond that connects two amino acids and is not an amide bond (—CONH—). A pseudopeptide bond may also be included in the amidated C-terminus. Any pseudopeptide bond known in the art is contemplated in the context of the present invention, for instance, —CH$_2$NH—, —CONRCH$_2$—, —CONCH— (the latter also referred to as N-Me), or —CONR—, wherein R is alkyl, preferably methyl, ethyl, n-propyl, isopropyl, n-butyl, s-butyl, isobutyl, t-butyl, n-pentyl, 1-methylbutyl, 2-methylbutyl, 3-methylbutyl, 1,1-dimethylpropyl, 1-methyl-2-methylpropyl, 2,2-dimethylpropyl, or 1-ethylpropyl.

Herein, the identity of the chemical bond between two amino acids may be indicated in parentheses or square brackets in between the amino acids that are connected through the bond, for instance, $X^4$-(N-Me)$X^5$. In this case, the two amino acids $X^4$ and $X^5$ are connected by a pseudopeptide bond of the structure —CONCH—, wherein the amide nitrogen is methylated. The following spellings, exemplarily given for two amino acids $X^4$ and $X^5$ and the pseudopeptide bond N-Me, are interchangeably used herein to indicate the nature of the pseudopeptide bond: "$X^4$-(N-Me)-$X^5$", "$X^4$-(N-Me)$X^5$" and "$X^4$(N-Me)-$X^5$". Alkylester, alkylether and urea bonds are also contemplated as pseudopeptide bonds. Other pseudopeptide bonds such as 1,2,3-triazoles (Mascarin A et al., Bioconjug Chem 2015, 26: 2143-2152) or other amide bond bioisosteres, which have shown to stabilize peptidomimetics and improve tumour targeting are also contemplated.

In some embodiments the presence of a pseudopeptide bond is indicated by the term "psi", as commonly used in the art. For instance, $X^4$-psi[CH$_2$NH]-$X^5$ indicates that the two amino acids $X^4$ and $X^5$ are connected via the pseudopeptide bond —CH$_2$NH—. In some embodiments the pseudopeptide bond can be -psi[CH$_2$—NH—CO—NH]-, -psi[CH$_2$—NH]-, -psi[CH$_2$—CH$_2$]—, -psi[CS—NH]- or -psi[Tz]-.

Further preferred pseudopeptide bonds are: —COO—, —COS—, —COCH$_2$—, —CSNH—, —CH$_2$CH$_2$—, —CHCH—, —CC—, —NHCO—, —CH$_2$S—, —CH$_2$—NH—CO—NH— and —CH$_2$O—.

In the context of the present invention L- and D-amino acids are equally contemplated. Any amino acid of the present invention may be present in L- or D-form unless otherwise stated.

The L-from is indicated by reciting a "L" directly before the name of the amino acid, the D-form is indicated by reciting a "D" directly before the name of the amino acid. For instance, "DGlu" refers to the D-form of the amino acid glutamate and "LGlu" refers to the L-form of the amino acid glutamate. In preferred embodiments, the enantiomeric form of one, more or all of the amino acids of the peptidomimetic is the L-form. For instance, if the nomenclature encompasses both enantiomeric forms, for example, as is the case in "-Asp-", then the preferred enantiomeric form is the L-form (as in "-LAsp-").

Cyclized forms of the peptidomimetic of the present invention are also contemplated, for example, the peptidomimetic may be cyclized by linking the N-terminus with the C-terminus, the N-terminus or side chain of the N-terminal amino acid with an amino acid side chain, or the C-terminus or side chain of the C-terminal amino acid with an amino acid side chain or two side chains of two different amino acids.

In some embodiments of the present invention the N-terminus is conjugated to a linker, spacer, chelator or prosthetic group and the C-terminus is amidated.

The term "chelator" is used as in the art and refers to organic compounds that are able to chelate metal ions.

The term "prosthetic group" also referred to as bifunctional labelling agent, is used as in the art and refers to a small organic molecule that can be easily radiolabelled, for example with a radionuclide, and conjugated to a biomolecule, such as an amino acid polymer, before or after radiolabelling, and is not a chelator. Generally, prosthetic groups are conjugated to amines, thiols or carboxylic acid functions present in the biomolecule. Also conjugation via click chemistry is contemplated.

In preferred embodiments of the present invention the C-terminus (carboxy terminus) of the peptidomimetic is modified to, for example, reduce proteolytic degradation, increase shelf life, and/or improve cellular uptake. The C-terminus may be for example amidated with an —NR'R" group, wherein R' and R" are independently hydrogen or a substituted or non-substituted alkyl as defined herein. In some embodiments R' and R" are independently ethyl, propyl, butyl, pentyl or hexyl. In some preferred embodiments the peptidomimetics of the present invention are amidated at the C-terminus with a —NH$_2$ group. The C-terminus can also be modified with an ester of the type —C(O)OR'", wherein R'" can be a substituted or non-substituted alkyl as defined herein, for instance, ethyl, propyl, butyl, pentyl or hexyl.

The term "alkyl" as used herein refers to a straight-chain or branched saturated aliphatic hydrocarbon with 1 to 20 (C1-C20), preferably 1 to 15 (C1-C15), more preferably 1 to 10 (C1-C10), and most preferably 1 to 5 (C1-05) carbon atoms. For example, "alkyl" may refer to methyl, ethyl, n-propyl, isopropyl, n-butyl, s-butyl, isobutyl, t-butyl, n-pentyl, 1-methylbutyl, 2-methylbutyl, 3-methylbutyl, 1,1-dimethylpropyl, 1-methyl-2-methylpropyl, 2,2-dimethylpropyl, and 1-ethylpropyl.

The "alkyl" group may be substituted with, for example, halogens, such as fluorine, chlorine and bromine, amines, such as a primary amine (—NH$_2$), primary amide, hydroxyl (—OH), further oxygen-, sulfur- or nitrogen-containing functional groups, heterocycles, or aryl substituents, such as phenyl and napthyl.

In a preferred embodiment (embodiment A), the enantiomeric form of Asp in $X^1$-$X^2$-Asp-$X^3$ (SEQ ID NO:3) of the peptidomimetic is the L-form ($X^1$—$X^2$-LAsp-$X^3$; SEQ ID NO:3).

In another preferred embodiment (embodiment B), the bond between $X^2$ and Asp of $X^1$-$X^2$-Asp-$X^3$ (SEQ ID NO:3) is not —CONCH— (N-Me, NMe).

In a further preferred embodiment (embodiment C), the bond between $X^2$ and Asp of $X^1$-$X^2$-Asp-$X^3$ (SEQ ID NO:3) is an amide bond.

In a preferred embodiment (embodiment D), the bond between $X^1$ and $X^2$ of $X^1$-$X^2$-Asp-$X^3$ (SEQ ID NO:3) is —CONCH— (N-Me, NMe).

In a preferred embodiment (embodiment E), $X^2$ is Nle.

Particularly preferred are embodiments (embodiment F), wherein the bond between $X^1$ and $X^2$ of $X^1$-$X^2$-Asp-$X^3$ (SEQ ID NO:3) is —CONCH— (N-Me, NMe) and $X^2$ is Nle.

In a preferred embodiment (embodiment G), the bond between $X^1$ and $X^2$ of $X^1$-$X^2$-Asp-$X^3$ (SEQ ID NO:3) is —CONCH— (N-Me, NMe), $X^2$ is Nle and $X^3$ is 1Nal or 2Nal, preferably 1Nal.

In another preferred embodiment (embodiment H) one or more of the amino acid residues in $X^4$-$X^5$-$X^6$-$X^7$ (SEQ ID NO:5) is Pro.

Particularly preferred are combinations of embodiment G with embodiments A, B, C or H.

The present invention encompasses peptidomimetics that are combinations of embodiments A-H, in particular, combinations of all embodiments A-H. These embodiments may be combined with any of the preceding or subsequent embodiments. In particular, any disclosed peptidomimetic that encompasses the sequence $X^1$-$X^2$-Asp-$X^3$ (SEQ ID NO:3) may be combined with embodiments A-H, or any combinations thereof.

Particularly preferred are embodiments, wherein $X^1$—$X^2$-Asp-$X^3$ (SEQ ID NO:3) is $X^1$-(N-Me)Nle-(CONH)-LAsp-$X^3$ (SEQ ID NO:3), and wherein $X^3$ is 1Nal or 2Nal.

In a preferred embodiment of the present invention, the peptidomimetic comprises an amino acid polymer with the sequence $X^4$-$X^5$-$X^6$-$X^7$-$X^1$-$X^2$-Asp-$X^3$ (SEQ ID NO:4). Preferably, the peptidomimetic comprises this polymer at the C-terminus of the peptidomimetic. More preferably, as mentioned above, the C-terminus of the peptidomimetic is amidated with a —NH$_2$ group. $X^4$ is Leu or another hydrophobic amino acid such as Pro or any proteinogenic charged amino acid, such as Arg, Asp, Lys, His and Glu. $X^5$ is Ala, beta-Ala, Tyr or Pro. $X^6$ is Tyr, Pro, Phe, Met or a hydrophobic unnatural amino acid with structural similarities to Met, such as Nle. $X^7$ is Gly, Thr, Ser, Ala, beta-Ala or Pro. Amino acids $X^1$, $X^2$ and $X^3$ are as defined herein. Any combination that results from the above or below mentioned embodiments of amino acids $X^4$, $X^5$, $X^6$, $X^7$, $X^1$, $X^2$, and $X^3$ is equally contemplated in the context of the present invention.

The peptidomimetic of the present invention comprises 5 to 50 amino acids. The term "comprises 5 to 50 amino acids" as used herein means that the peptidomimetic does not have more than 50 amino acids and not less than 5 amino acids. In addition, the comprising language ("comprising") means that the peptidomimetic may contain further components, such as a chelator, a prosthetic group, a linker, a spacer, a pharmacokinetic modifier, a reporter group or cytotoxic group, that are not explicitly recited.

In some embodiments the peptidomimetic comprises not more than 45, 40, 35, 30, 25, 20, 15 or 13 amino acids. Particularly preferred are peptidomimetics that comprise 5 to 15 amino acids. More preferred are peptidomimetics that comprise 8 to 13 amino acids. In some embodiments of the present invention, the peptidomimetic comprises at least 6, 7, 8, 9, 10, 11, 12, 13, 14 or 15 amino acids. Any range that results from a combination of the above mentioned maximal and minimal numbers of amino acids that are comprised by the peptidomimetic is also contemplated in the context of the present invention, for instance, in some embodiments the peptidomimetic comprises 8 to 35, 8 to 25 or 8 to 20 amino acids. Equally contemplated are the above-mentioned ranges wherein both the upper and the lower endpoint of the range is excluded, both the upper and the lower endpoint of the range is included, wherein the lower endpoint is included and the upper endpoint is excluded, or wherein the lower endpoint is excluded and the upper endpoint is included. This interpretation applies to all ranges recited in the present application.

In some preferred embodiments of the present invention, the peptidomimetic comprises 8 to 13 amino acids, $X^1$ is Trp, $X^2$ is Nle, and $X^3$ is 1Nal or 2Nal. In even more preferred embodiments of the present invention, the peptidomimetic comprises 8 to 13 amino acids, $X^1$ is Trp, $X^2$ is Nle, $X^3$ is 1Nal or 2Nal, the bond between $X^1$ and $X^2$ is —CONCH$_3$—, and the C-terminus is amidated with a —NH$_2$ group. In a further preferred embodiment, the peptidomimetic comprises 8 to 13 amino acids, $X^1$ is Trp, $X^2$ is Nle, $X^3$ is 1Nal or 2Nal, the bond between $X^1$ and $X^2$ is —CONCH$_3$—, Asp in $X^1$-$X^2$-Asp-$X^3$ is in the L-form, the bond between $X^2$ and Asp is an amide bond (—CONH—) and the C-terminus is amidated with a —NH$_2$ group Preferably, these and all other peptidomimetics mentioned herein are modified at the N-terminus with the chelator DOTA or HYNIC.

In some embodiments of the present invention $X^1$ is a hydrophobic amino acid. Preferably, $X^1$ is Phe or Trp. Most preferably, $X^1$ is Trp.

In some embodiments of the present invention $X^2$ is a hydrophobic amino acid with structural similarity to Met. Preferably, $X^2$ is Leu or Nle. Most preferably, $X^2$ is Nle.

In some embodiments of the present invention $X^3$ is an unnatural hydrophobic amino acid with structural similarity to Phe. Preferably, $X^3$ is 1Nal or 2Nal. Most preferably, $X^3$ is 1Nal.

In some embodiments of the present invention $X^4$ is Leu or another hydrophobic amino acid such as Pro or a proteinogenic charged amino acid. Preferably, $X^4$ is Leu, Arg, Asp, Asn, Lys, His or Glu. Preferably, $X^4$ is an amino acid in D form. Most preferably, $X^4$ is DGlu or DLys, in particular DGlu.

In some embodiments of the present invention $X^5$ is Ala, beta-Ala, Tyr or Pro. Preferably, $X^5$ is Ala, Tyr or Pro.

In some embodiments of the present invention $X^6$ is Tyr, Pro, Phe, Met, or a hydrophobic amino acid with structural similarity to Met, such as Leu or Nle. Preferably, $X^6$ is Tyr or Pro.

In some embodiments of the present invention $X^7$ is Gly, Thr, Ser, Ala, beta-Ala or Pro. Preferably, $X^7$ is Gly or Pro.

The following tables list particularly preferred embodiments of the present invention. Particularly preferred are peptidomimetics that comprise or consist of amino acid polymers with the sequences listed in Table 1. In preferred embodiments of the present invention the amino acid polymer listed in Table 1 is located at the C-terminus of the peptidomimetic, preferably the C-terminus is amidated.

TABLE 1

DGlu-Ala-Tyr-Gly-Trp-(N-Me)Nle-Asp-1Nal

DGlu-Ala-Tyr-Gly-Trp-(N-Me)Nle-Asp-2Nal

DGlu-Pro-Tyr-Gly-Trp-(N-Me)Nle-Asp-$X^3$

DLys-Ala-Tyr-Gly-Trp-(N-Me)Nle-Asp-$X^3$

DGlu-Tyr-Pro-Gly-Trp-(N-Me)Nle-Asp-$X^3$

DGlu-$X^5$-$X^6$-Gly-Trp-(N-Me)Nle-Asp-$X^3$

DGlu-$X^5$-$X^6$-Gly-Trp-(N-Me)Nle-Asp-(N-Me)$X^3$

DGlu-$X^5$-$X^6$-Gly-Trp-(N-Me)Nle-Asp-$X^3$-psi[CH$_2$NH$_2$]

DGlu-$X^5$-$X^6$-Gly-Trp-(N-Me)Nle-Asp-psi[CH$_2$NH]-$X^3$

DGlu-$X^5$-$X^6$-Gly-Trp-(N-Me)Nle-psi[CH$_2$NH]Asp-$X^3$

TABLE 1-continued

DGlu-X⁵-X⁶-Gly-Trp-psi[CH₂NH]-Nle-Asp-X³

DGlu-X⁵-X⁶-Gly-Trp-psi[CH₂NH]-Nle-Asp-(N-Me)X³

DGlu-X⁵-X⁶-Gly-psi[CH₂NH]-Trp-psi[CH₂NH]-Nle-psi[CH₂NH]-Asp-psi[CH₂NH]-X³

DGlu-X⁵-psi[CH₂NH]-X⁶-Gly-Trp-(N-Me)Nle-Asp-X³

DGlu-X⁵-X⁶-psi[CH₂NH]-Gly-Trp-(N-Me)Nle-Asp-X³

DGlu-X⁵-X⁶-Gly-psi[CH₂NH]-Trp-(N-Me)Nle-Asp-X³

DGlu-X⁵-X⁶-Gly-Trp-psi[CH₂NH]-(N-Me)Nle-Asp-X³

DGlu-X⁵-X⁶-(N-Me)Gly-Trp-(N-Me)Nle-Asp-X³

DGlu-X⁵-X⁶-Thr-Trp-(N-Me)Nle-Asp-X³

DGlu-X⁵-X⁶-Ser-Trp-(N-Me)Nle-Asp-X³

DGlu-X⁵-X⁶-Gly-DPhe-(N-Me)Nle-Asp-X³

DGlu-X⁵-X⁶-DGly-Phe-(N-Me)Nle-Asp-X³

DGlu-(DGlu)₅-X⁵-X⁶-Gly-Trp-(N-Me)Nle-Asp-X³-NH₂

DGlu-(Glu)₅-X⁵-X⁶-Gly-Trp-(N-Me)Nle-Asp-X³-NH₂

DAsp-X⁵-X⁶-Gly-Trp-(N-Me)Nle-Asp-X³-NH₂

DGlu-Ala-Tyr-Pro-Trp-(N-Me)Nle-Asp-X³

TABLE 1-continued

Pro-Ala-Tyr-Gly-Trp-(N-Me)Nle-Asp-X³ (SEQ ID NO: 6)

Leu-Ala-Tyr-Gly-Trp-(N-Me)Nle-Asp-X³ (SEQ ID NO: 7)

X⁴-Ala-Tyr-Gly-Trp-(N-Me)Nle-Asp-X³ (SEQ ID NO: 8)

DGlu-X⁵-X⁶-X⁷-Trp-(N-Me)Nle-Asp-X³

DGlu-Ala-Tyr-Gly-(N-Me)Trp-(N-Me)Nle-Asp-X³

DGlu-Ala-(N-Me)Tyr-Gly-Trp-(N-Me)Nle-Asp-X³

DGlu-(N-Me)Ala-Tyr-Gly-Trp-(N-Me)Nle-Asp-X³

(N-Me)DGlu-Ala-Tyr-Gly-Trp-(N-Me)Nle-Asp-X³

DGlu-Ala-Tyr-Gly-DTrp-(N-Me)Nle-Asp-X³

Equally contemplated are peptidomimetics that comprise at least the 4 most C-terminal amino acids of the amino acid polymer sequences of Table 1 and which comprise 5 to 50 amino acids, preferably 8 to 13 amino acids.

In some embodiments of the present invention the peptidomimetic comprises a chelator. In some embodiments the chelator is DOTA or HYNIC. Table 2, shown below, illustrates some preferred embodiments of the present invention. In some embodiments of the present invention, the peptidomimetic may comprise one of the structures as shown in Table 2, or may consist of one of the structures as shown in Table 2.

TABLE 2

DOTA-DGlu-Ala-Tyr-Gly-Trp-(N-Me)Nle-Asp-X³-NH₂

HYNIC-DGlu-Ala-Tyr-Gly-Trp-(N-Me)Nle-Asp-X³-NH₂

DOTA-DGlu-Pro-Tyr-Gly-Trp-(N-Me)Nle-Asp-X³-NH₂

DOTA-DLys-Ala-Tyr-Gly-Trp-(N-Me)Nle-Asp-X³-NH₂

DOTA-DGlu-Tyr-Pro-Gly-Trp-(N-Me)Nle-Asp-X³-NH₂

DOTA-DGlu-Ala-Tyr-Pro-Trp-(N-Me)Nle-Asp-X³-NH₂

DOTA-DGlu-Ala-Tyr-(N-Me)Gly-Trp-(N-Me)Nle-Asp-X³-NH₂

DOTA-DGlu-Ala-Tyr-Gly-DTrp-(N-Me)Nle-Asp-X³-NH₂

DOTA-DGlu-X⁵-X⁶-Gly-Trp-(N-Me)Nle-Asp-X³-NR'R"
(R' and R" = alkyl as defined herein)

DOTA-DGlu-X⁵-X⁶-Gly-Trp-(N-Me)Nle-Asp-(N-Me)X³-NH₂

DOTA-DGlu-X⁵-X⁶-Gly-Trp-(N-Me)Nle-Asp-X³-psi[CH₂NH₂]

DOTA-DGlu-X⁵-X⁶-Gly-Trp-(N-Me)Nle-Asp-psi[CH₂NH]-X³-NH₂

DOTA-DGlu-X⁵-X⁶-Gly-Trp-(N-Me)Nle-psi[CH₂NH]Asp-X³-NH₂

DOTA-DGlu-X⁵-X⁶-Gly-Trp-psi[CH₂NH]-Nle-Asp-X³-NH₂

DOTA-DGlu-X⁵-X⁶-Gly-Trp-psi[CH₂NH]-Nle-Asp-(N-Me)X³-NH₂

DOTA-DGlu-X⁵-X⁶-Gly-psi[CH₂NH]-Trp-psi[CH₂NH]-Nle-psi[CH₂NH]-Asp-psi[CH₂NH]-X³-NH₂

DOTA-DGlu-X⁵-psi[CH₂NH]-X⁶-Gly-Trp-(N-Me)Nle-Asp-X³-NH₂

DOTA-DGlu-X⁵-X⁶-psi[CH₂NH]-Gly-Trp-(N-Me)Nle-Asp-X³-NH₂

DOTA-DGlu-X⁵-X⁶-Gly-psi[CH₂NH]-Trp-(N-Me)Nle-Asp-X³-NH₂

DOTA-DGlu-X⁵-X⁶-Gly-Trp-psi[CH₂NH]-(N-Me)Nle-Asp-X³-NH₂

TABLE 2-continued

DOTA-DGlu-X⁵-X⁶-(N-Me)Gly-Trp-(N-Me)Nle-Asp-X³-NH₂

DOTA-DGlu-X⁵-X⁶-Thr-Trp-(N-Me)Nle-Asp-X³-NH₂

DOTA-DGlu-X⁵-X⁶-Ser-Trp-(N-Me)Nle-Asp-X³-NH₂

DOTA-DGlu-X⁵-X⁶-Gly-DPhe-(N-Me)Nle-Asp-X³-NH₂

DOTA-DGlu-X⁵-X⁶-DGly-Phe-(N-Me)Nle-Asp-X³-NH₂

DOTA-DGlu-(DGlu)₅-X⁵-X⁶-Gly-Trp-(N-Me)Nle-Asp-X³-NH₂

DOTA-DGlu-(Glu)₅-X⁵-X⁶-Gly-Trp-(N-Me)Nle-Asp-X³-NH₂

DOTA-DAsp-Tyr-X⁶-Gly-Trp-(N-Me)Nle-Asp-X³-NH₂

DOTA-X⁴-Ala-Tyr-Gly-Trp-(N-Me)Nle-Asp-X³-NH₂ (SEQ ID NO: 9)

DOTA-X⁴-X⁵-Tyr-Gly-Trp-(N-Me)Nle-Asp-X³-NH₂ (SEQ ID NO: 10)

DOTA-X⁴-X⁵-X⁶-Gly-Trp-(N-Me)Nle-Asp-X³-NH₂ (SEQ ID NO: 11)

DOTA-X⁴-X⁵-X⁶-X⁷-Trp-(N-Me)Nle-Asp-X³-NH₂ (SEQ ID NO: 12)

DOTA-X⁴-X⁵-X⁶-X⁷-(N-Me)Trp-(N-Me)Nle-Asp-X³-NH₂ (SEQ ID NO: 13)

DOTA-X⁴-X⁵-X⁶-(N-Me)Gly-Trp-(N-Me)Nle-Asp-X³-NH₂ (SEQ ID NO: 14)

DOTA-DGlu-X⁵-(N-Me)X⁶-Gly-Trp-(N-Me)Nle-Asp-X³-NH₂

DOTA-X⁴-(N-Me)X⁵-X⁶-Gly-Trp-(N-Me)Nle-Asp-X³-NH₂ (SEQ ID NO: 15)

DOTA-(N-Me)X⁴-X⁵-X⁶-Gly-Trp-(N-Me)Nle-Asp-X³-NH₂ (SEQ ID NO: 16)

$X^3$ as recited in Table 1 or 2 is as used herein, preferably 1Nal or 2Nal, most preferably 1Nal.

$X^4$, $X^5$, $X^6$, and $X^7$ as recited in Table 1 or 2 is as used herein, in particular, $X^4$ is Leu or another hydrophobic amino acid such as Pro or any proteinogenic charged amino acid such as Arg, Asp, Lys, His and Glu, $X^5$ is Ala, beta-Ala, Tyr or Pro, and $X^6$ is Tyr, Pro, Phe, Met or a hydrophobic amino acid with structural similarity to Met, such as Leu or Nle, and $X^7$ is Gly, Thr, Ser, Ala, beta-Ala or Pro.

It should be understood, that the peptidomimetics listed in Tables 1 and 2 are given by way of illustration and that combinations of the different modifications stated in Table 1 or 2 which are not explicitly disclosed are also contemplated. Preferred embodiments of Tables 1 and 2 are given in Table 3 below.

TABLE 3

DOTA-DGlu-Ala-Tyr-Gly-Trp-(N-Me)Nle-Asp-1Nal-NH₂

HYNIC-DGlu-Ala-Tyr-Gly-Trp-(N-Me)Nle-Asp-1Nal-NH₂

DOTA-DGlu-Ala-Tyr-Gly-Trp-(N-Me)Nle-Asp-2Nal-NH₂

DOTA-DGlu-Pro-Tyr-Gly-Trp-(N-Me)Nle-Asp-1Nal-NH₂

DOTA-DLys-Ala-Tyr-Gly-Trp-(N-Me)Nle-Asp-1Nal-NH₂

DOTA-DGlu-Tyr-Pro-Gly-Trp-(N-Me)Nle-Asp-1Nal-NH₂

DGlu-Ala-Tyr-Gly-Trp-(N-Me)Nle-Asp-1Nal-NH₂

DGlu-Ala-Tyr-Gly-Trp-(N-Me)Nle-Asp-2Nal-NH₂

DGlu-Pro-Tyr-Gly-Trp-(N-Me)Nle-Asp-1Nal-NH₂

DLys-Ala-Tyr-Gly-Trp-(N-Me)Nle-Asp-1Nal-NH₂

DGlu-Tyr-Pro-Gly-Trp-(N-Me)Nle-Asp-1Nal-NH₂

TABLE 3-continued

DOTA-DGlu-Ala-Tyr-Gly-Trp-(N-Me)Nle-Asp-(N-Me)1Nal-NH₂

HYNIC-DGlu-Ala-Tyr-Gly-Trp-(N-Me)Nle-Asp-(N-Me)1Nal-NH₂

DOTA-DGlu-Ala-Tyr-Pro-Trp-(N-Me)Nle-Asp-1Nal-NH₂

DGlu-Ala-Tyr-Gly-Trp-(N-Me)Nle-Asp-(N-Me)1Nal-NH₂

DGlu-Ala-Tyr-Pro-Trp-(N-Me)Nle-Asp-1Nal-NH₂

In Tables 1-3, unless otherwise indicated, the individual amino acids are linked through amide bonds. Preferably, any amino acid shown in Tables 1-3 is in the L-form, for example, Asp in Tables 1-3 is preferably LAsp.

In some embodiments of the present invention the peptidomimetic comprises one of the structures as shown in Table 2 or 3, wherein the chelator DOTA or HYNIC coordinates a radionuclide, for example a metal radionuclide, such as $^{225}$Ac, $^{212}$Bi, $^{213}$Bi, $^{62}$Cu, $^{64}$Cu, $^{67}$Cu, $^{69}$Cu, $^{66}$Ga, $^{67}$Ga, $^{68}$Ga, $^{111}$In, $^{113m}$In, $^{177}$Lu, $^{186}$Re, $^{188}$Re, $^{43}$Sc, $^{44}$Sc, $^{47}$Sc, $^{155}$Tb, $^{161}$Tb, $^{99m}$Tc, $^{86}$Y, $^{90}$Y, $^{169}$Yb, $^{175}$Yb.

In particularly preferred embodiments of the present invention, the peptidomimetic consists of the structures as shown in Table 2 or 3, wherein in addition to the information provided in Table 2 or 3 the DOTA chelator coordinates the radionuclide $^{90}$Y, $^{111}$In, $^{68}$Ga or $^{177}$Lu and the HYNIC chelator coordinates the radionuclide $^{99m}$Tc.

The peptidomimetics of the present invention may comprise a reporter group, a cytotoxic group, a photosensitizer, a linker and/or a pharmacokinetic modifier. Preferably, the peptidomimetics comprise a reporter group or a cytotoxic group.

Reporter Group

The term "reporter group" as used herein can be any material or chemical moiety capable of being detected either directly or indirectly in a method of imaging. Peptidomimetics that comprise a reporter group can therefore be used in methods of imaging, for instance, for diagnostic purposes. The term "reporter group" is interchangeably used with the terms "reporter agent" and "label". The reporter group can be a material or chemical moiety that emits or may be caused to emit detectable radiation (e.g. by radioactive decay, fluorescence excitation, spin resonance excitation, etc.), affects local electromagnetic fields (e.g. paramagnetic, superparamagnetic, ferrimagnetic or ferromagnetic species), absorbs or scatters radiation energy (e.g. chromophores and fluorophores), particles (including liquid containing vesicles), heavy elements and compounds thereof, and moieties which generate a detectable substance, and others.

A wide range of materials and chemical moieties that are detectable by methods of imaging, for example diagnostic methods of imaging, such as computer tomography (CT), magnetic resonance imaging (MRI), scintigraphy, SPECT, PET, or other similar techniques, are known from the art and the reporter group will be selected according to the method of imaging to be used. Thus, for example, for ultrasound imaging an echogenic material, or a material capable of generating an echogenic material will normally be selected.

The reporter group may be a fluorophore. Fluorophores as defined herein are known in the art and available to the skilled person and include and are not limited to all the various members of the alexa family, bimane, bodipy, nitrobenzoxadiazole, dansyl, acrylodan, fluorescein, rhodamine, lanthanides, and members of the Cye3/Cye5 series (Filizola M, G Protein-Coupled Receptors in Drug Discovery, Humana Press, Springer Science+Business Media New York 2015). Preferred fluorophores are, for instance, near infrared dyes, such as, indocyanine green, IRDye 800CW, IRDye 650, LS-288, or Alexa Fluor dyes (for instance AF647, AF680 and AF488), fluorescein, cyanine and hemicyanine dyes, such as Dy488, Dy676 and Dy754. These fluorophores can be, for example, used in methods of imaging in the context of fluorescence microscopy or fluorescence guided endoscopy or surgery and optical imaging. The reporter group may also be a chemiluminescent dye.

The reporter group may also be a stable isotope or a chemical moiety comprising a stable isotope.

The reporter group may further be or contain a heavy atom (e.g. of atomic weight 38 or above), in particular for being detected by x-ray imaging. The reporter group may also be a non zero nuclear spin isotope (such as $^{19}F$) or a material having unpaired electron spins and hence paramagnetic, superparamagnetic, ferrimagnetic or ferromagnetic properties, which is useful for magnetic resonance imaging. The reporter group can be a light scatterer (e.g. a coloured or uncoloured particle), a light absorber or a light emitter, which is useful for light imaging. For magnetometric imaging the reporter group will have detectable magnetic properties; for electrical impedance imaging the reporter group will affect electrical impedance. The reporter group can be a radionuclide or a chemical moiety comprising a radionuclide, which is useful for scintigraphy, SPECT, PET, or other similar techniques.

Examples of suitable reporter groups that can be used in the context of the present invention are widely known from the diagnostic imaging literature, e.g. magnetic iron oxide particles, X-ray contrast agent containing vesicles, chelated paramagnetic metals (such as Gd, Dy, Mn, Fe etc.). See for example U.S. Pat. No. 4,647,447, PCT/GB97/00067, U.S. Pat. Nos. 4,863,715, 4,770,183, WO96/09840, WO85/02772, WO92/17212, PCT/GB97/00459, EP-A-554213, U.S. Pat. No. 5,228,446, WO91/15243, WO93/05818, WO96/23524, WO96/17628, U.S. Pat. No. 5,387,080, WO95/26205, and GB9624918.0. See also WO 98/47541 (pages 63-66 and 70-86).

Particularly preferred as reporter group are chelated paramagnetic metal ions such as Gd, Dy, Fe, and Mn, especially when chelated by macrocyclic chelators.

The reporter group may be (1) a chelatable metal or polyatomic metal-containing ion (i.e. TcO, etc), where the metal is a high atomic number metal (e.g. atomic number greater than 37), a paramagnetic species (e.g. a transition metal or lanthanide), or a radioactive isotope, (2) a covalently bound non-metal species which is an unpaired electron site (e.g. an oxygen or carbon in a persistent free radical), a high atomic number non-metal, or a radioisotope, (3) a polyatomic cluster or crystal containing high atomic number atoms, displaying cooperative magnetic behavior (e.g. superparamagnetism, ferrimagnetism or ferromagnetism) or containing radionuclides, or (4) a chromophore (by which term species which are fluorescent or phosphorescent are included), e.g. an inorganic or organic structure, particularly a complexed metal ion or an organic group having an extensive delocalized electron system.

Examples of particular preferred reporter groups are described in more detail below.

Preferred reporter groups are, for instance, radionuclides, such as metal radionuclides, paramagnetic metal ions, fluorescent metal ions, heavy metal ions and cluster ions.

The radionuclide of the present invention can be selected, for example, from radioisotopes of C, N, O F, Na, P, Sc, Ti, Cr, Mn, Fe, Co, Cu, Zn, Ga, Ge, As, Se, Br, Rb, Sr, Y, Zr, Mo, Tc, Ru, Rh, Pd, Ag, In, Sn, Sb, Te, I, La, Ce, Pr, Pm, Sm, Gd, Tb, Dy, Ho, Er, Tm, Yb, Lu, Ta, W, Re, Os, Ir, Pt, Au, Hg, Tl, Pb, Bi, Po, At, Ra, Ac, Th, and Fm.

Preferred radionuclides include, but are not limited to radionuclides of metals, such as but not limited to $^{225}Ac$, $^{198}Au$, $^{199}Au$, $^{212}Bi$, $^{213}Bi$, $^{51}Cr$, $^{62}Cu$, $^{64}Cu$, $^{67}Cu$, $^{69}Cu$, $^{159}Dy$, $^{166}Dy$, $^{66}Ga$, $^{67}Ga$, $^{68}Ga$, $^{159}Gd$, $^{166}Ho$, $^{111}In$, $^{113m}In$, $^{196}Ir$, $^{177}Lu$, $^{189m}Os$, $^{203}Pb$, $^{109}Pd$, $^{149}Pm$, $^{151}Pm$, $^{142}Pr$, $^{143}Pr$, $^{186}Re$, $^{188}Re$, $^{97}Ru$, $^{43}Sc$, $^{44}Sc$, $^{47}Sc$, $^{153}Sm$, $^{117m}Sn$, $^{121}Sn$, $^{155}Tb$, $^{161}Tb$, $^{99m}Tc$, $^{127}Te$, $^{167}Tm$, $^{86}Y$, $^{90}Y$, $^{169}Yb$, $^{175}Yb$, and $^{89}Zr$. Preferred reporter groups are radionuclides of halogens, such as, but not limited to $^{18}F$, $^{131}I$, $^{123}I$, $^{124}I$, and $^{125}I$.

Gamma and positron emitters for diagnostic applications include and are not limited to 11C, $^{51}Cr$, $^{62}Cu$, $^{64}Cu$, $^{52}Fe$, $^{66}Ga$, $^{67}Ga$, $^{68}Ga$, $^{123}I$, $^{124}I$, $^{125}I$, $^{111}In$, $^{113m}In$, $^{177}Lu$, $^{24}Na$, $^{203}Pb$, $^{97}Ru$, $^{43}Sc$, $^{44}Sc$, $^{152}Tb$, $^{155}Tb$, $^{94m}Tc$, $^{99m}Tc$, $^{167}Tm$, $^{86}Y$, and $^{89}Zr$.

Radionuclides with alpha and beta emission as well as Auger electron and internal conversion electron emission for therapeutic applications include and are not limited to $^{225}Ac$, $^{111}Ag$, $^{77}As$, $^{211}At$, $^{198}Au$, $^{199}Au$, $^{212}Bi$, $^{213}Bi$, $^{77}Br$, $^{58}Co$, $^{51}Cr$, $^{67}Cu$, $^{152}Dy$, $^{159}Dy$, $^{165}Dy$, $^{169}Er$, $^{255}Fm$, $^{67}Ga$, $^{159}Gd$, $^{195}Hg$, $^{161}Ho$, $^{166}Ho$, $^{123}I$, $^{125}I$, $^{131}I$, $^{111}In$, $^{192}Ir$, $^{194}Ir$, $^{196}Ir$, $^{177}Lu$, $^{189m}Os$, $^{32}P$, $^{212}Pb$, $^{109}Pd$, $^{149}Pm$, $^{142}Pr$, $^{143}Pr$, $^{223}Ra$, $^{186}Re$, $^{188}Re$, $^{105}Rh$, $^{119}Sb$, $^{47}Sc$, $^{153}Sm$, $^{117m}Sn$, $^{121}Sn$, $^{89}Sr$, $^{149}Tb$, $^{161}Tb$, $^{99m}Tc$, $^{127}Te$, $^{227}Th$, $^{201}Tl$, and $^{90}Y$. Preferred paramagnetic metal ions include and are not limited to ions of transition and lanthanide metals (e.g. metals having atomic numbers of 6 to 9, 21-29, 42, 43, 44, or 57-71), in particular ions of Cr, V, Mn, Fe, Co, Ni, Cu, La, Ce, Pr, Nd, Pm, Sm, Eu, Gd, Tb, Dy, Ho, Er, Tm, Yb and Lu, especially of Mn, Cr, Fe, Gd and Dy, more especially Gd.

In some embodiments of the present invention, the reporter group has no therapeutic effect, such as a cytotoxic effect, in particular when comprised by the peptidomimetic. In some embodiments, the reporter group does at least not have a cytotoxic effect to a degree that is therapeutically relevant. The skilled person is able to determine an administered dose/radioactivity dose of the reporter group that is sufficient for being detected, for instance in a method of imaging, but low enough for not having a therapeutic effect. Consequently, in some embodiments of the present invention, for instance, the method of imaging and any diagnostic uses or methods, a dose of the reporter group, in particular the radionuclide, is used that is sufficient for detection, but does not have a therapeutic effect. As used herein, reporter groups without therapeutic effect are referred to as "non-therapeutic reporter groups". Thus, the present invention also relates to non-therapeutic embodiments of the above mentioned reporter groups. For example the invention includes non-therapeutic fluorophores, stable isotopes or chemical moieties comprising a stable isotope, heavy atoms, radionuclides, such as metal radionuclides, paramagnetic metal ions, fluorescent metal ions, heavy metal ions and cluster ions.

Preferred non-therapeutic reporter groups that are radionuclides, which can be used for imaging, are $^{64}$Cu, $^{67}$Ga, $^{68}$Ga, $^{123}$I, $^{124}$I, $^{125}$I, $^{131}$I, $^{111}$In, $^{177}$Lu, $^{203}$Pb, $^{97}$Ru, $^{44}$Sc, $^{152}$Tb, $^{155}$Tb, $^{99m}$Tc, $^{167}$Tm, $^{86}$Y, and $^{89}$Zr.

Cytotoxic Group

In some embodiments, the peptidomimetic comprises a cytotoxic group. The term "cytotoxic group" as used herein refers to any material or chemical moiety that directly or indirectly causes the death of the cell to which the peptidomimetic that comprises the cytotoxic group is bound or by which it has been internalized.

The cytotoxic group can be, for example, a chemotherapeutic agent or a radionuclide. If the chemotherapeutic agent or radionuclide that is comprised by the peptidomimetic is internalized by a cell that expresses CCK2R, the CCK2R expressing cell is killed by the chemotherapeutic agent or radionuclide. In some embodiments, the cell to which the peptidomimetic is bound may also be killed without internalizing the peptidomimetic that comprises the cytotoxic group.

The chemotherapeutic agent can be selected from the group consisting of vinblastine monohydrazide, tubulysin B hydrazide, actinomycin, all-trans retinoic acid, azacitidine, bleomycin, bortezomib, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, irinotecan, mechlorethamine, mercaptopurine, methotrexate, mitoxantrone, oxaliplatin, paclitaxel, pemetrexed, teniposide, tioguanine, topotecan, indotecan, indimitecan, mertansine, emtansine, valrubicin, vemurafenib, vinblastine, vincristine, vindesine, and vinorelbine.

Preferred radionuclides that can be used as a cytotoxic group include metal and halogen radionuclides. The radionuclide of the present invention can be for example selected from radioisotopes of P, Sc, Cr, Mn, Fe, Co, Cu, Zn, Ga, As, Br, Sr, Y, Tc, Ru, Rh, Pd, Ag, In, Sn, Sb, Te, I, Pr, Pm, Sm, Gd, Tb, Y, Ho, Er, Lu, Ta, W, Re, Os, Ir, Au, Hg, Tl, Pb, Bi, Po, At, Ra, Ac, Th, and Fm. Preferred radionuclides include, but are not limited to, $^{225}$Ac, $^{111}$Ag, $^{77}$As, $^{211}$At, $^{198}$Au, $^{199}$Au, $^{212}$Bi, $^{213}$Bi, $^{77}$Br, $^{58}$Co, $^{51}$Cr, $^{67}$Cu, $^{152}$Dy, $^{159}$Dy, $^{165}$Dy, $^{169}$Er, $^{255}$Fm, $^{67}$Ga, $^{159}$Gd, $^{195}$Hg, $^{161}$Ho, $^{166}$Ho, $^{123}$I, $^{125}$I, $^{131}$I, $^{111}$In, $^{192}$Ir, $^{194}$Ir, $^{196}$Ir, $^{177}$Lu, $^{189m}$Os, $^{32}$P, $^{212}$Pb, $^{109}$Pd, $^{149}$Pm, $^{142}$Pr, $^{143}$Pr, $^{223}$Ra, $^{186}$Re, $^{188}$Re, $^{105}$Rh, $^{119}$Sb, $^{47}$Sc, $^{153}$Sm, $^{117m}$Sn, $^{121}$Sn, $^{89}$Sr, $^{149}$Tb, $^{161}$Tb, $^{99m}$Tc, $^{127}$Te, $^{227}$Th, $^{201}$Tl, and $^{90}$Y.

Photosensitizer

In some embodiments of the present invention the peptidomimetic comprises a photosensitizer.

As used herein the term "photosensitizer" refers to a material or chemical moiety that becomes toxic or releases toxic substances upon exposure to light such as singlet oxygen or other oxidizing radicals which are damaging to cellular material or biomolecules, including the membranes of cells and cell structures, and such cellular or membrane damage may eventually kill the cells. Photosensitizers as defined herein are known in the art and available to the skilled person. The cytotoxic effects of photosensitizers can be used in the treatment of various abnormalities or disorders, including neoplastic diseases. Such treatment is known as photodynamic therapy (PDT) and involves the administration of a photosensitizer to the affected area of the body, followed by exposure to activating light in order to activate the photosensitizer and convert them into cytotoxic form, whereby the affected cells are killed or their proliferative potential diminished.

Photosensitizers exert their effects by a variety of mechanisms, directly or indirectly. Thus for example, certain photosensitizers become directly toxic when activated by light, whereas other photosensitizers act to generate toxic species, e.g. oxidizing agents such as singlet oxygen or oxygen-derived free radicals, which are destructive to cellular material and biomolecules, such as lipids, proteins and nucleic acids, and ultimately kill cells.

In some embodiments the photosensitizer includes, for example, psoralens, porphyrins, chlorins and phthalocyanines. Porphyrin photosensitizers act indirectly by generation of toxic oxygen species and are particularly preferred. Porphyrins are naturally occurring precursors in the synthesis of heme. In particular, heme is produced when iron ($Fe^{2+}$) is incorporated in protoporphyrin IX (PpIX) by the action of the enzyme ferrochelatase. PpIX is a highly potent photosensitizer. Further photosensitizer that can be used in the context of the present invention are aminolevulinic acid (ALA), silicon phthalocyanine Pc 4, m-tetrahydroxyphenyl-chlorin (mTHPC) and mono-L-aspartyl chlorin e6 (NPe6), porfimer sodium, verteporfin, temoporfin, methyl aminolevulinate, hexyl aminolevulinate, laserphyrin-PDT, BF-200 ALA, amphinex and azadipyrromethenes.

Linker

The peptidomimetic of the present invention comprises an amino acid polymer with a sequence as defined herein. The total number of amino acids comprised by the peptidomimetic is limited as defined herein. In addition to the amino acid polymer, the peptidomimetic of the present invention may comprise further components, such as a reporter group, a cytotoxic group, a photosensitizer, a chelator, a prosthetic group, a pharmacokinetic modifier, a linker, or a spacer. These individual components or chemical moieties may be directly connected to each other or to the amino acid polymer through a covalent, ionic or coordinated bond, for example, the reporter group or the cytotoxic group may be connected with a chelator through a coordinated bond.

Alternatively, the above-mentioned components may be indirectly connected to each other or to the amino acid polymer through a linker. The term "linker" as used herein refers to a chemical moiety that connects two individual chemical moieties. The terms "linker" or "spacer" are interchangeably used in the literature and herein to describe such a chemical moiety. The linker can be bound to the N-terminus of the amino acid polymer of the peptidomimetic, integrated within the amino acid sequence of the amino acid polymer of the peptidomimetic or conjugated to a side chain of an amino acid of the amino acid polymer of the peptidomimetic or another functional group and is usually used as a separator between the amino acid polymer of the peptidomimetic and the reporter agent or cytotoxic agent or as pharmacokinetic modifier influencing, for example, the hydrophilicity and pharmacokinetics of the peptidomimetic. For example, the reporter group, the cytotoxic group, the photosensitizer, the chelator, the prosthetic group or the pharmacokinetic modifier of the present invention may be connected with the amino acid polymer, for instance $X^4$-$X^5$-$X^6$-$X^7$-$X^1$-$X^2$-Asp-$X^3$ (SEQ ID NO:4), through a linker. The linker can connect any of the above mentioned components to the N-terminus, the C-terminus or any side chain of the amino acid polymer of the peptidomimetic. In some embodiments, the linker may also connect the above mentioned components with each other, for instance, the linker may connect a pharmacokinetic modifier with the reporter group.

The linker may be an amino acid, such as Gly, Ala, Gln, Glu, His, all in L- or D-form, or an amino acid polymer consisting of one or more of these amino acids, or any other chemical moiety, such as polyethylene glycol or a carbohydrate, as well as aminohexanoyl or aminobenzoyl or piperidine moieties. In some embodiments the linker can be 6-aminohexanoic acid, 4-aminobutyric acid, 4-amino-1-carboxymethylpiperidine or urea or another chemical moiety that allows introducing a functional group in the peptidomimetic. In some embodiments the linker is a combination of the above mentioned linkers.

The linker can be used as a separator of the individual components of the peptidomimetic. The linker can also be used to form multimeric conjugates of multiple peptidomimetics or in combination with other ligands targeting for instance alternative receptors. The linker can further be used to bind multiple reporter groups or a combination of a reporter group and a cytotoxic group to the peptide. Such examples are given by the divalent gastrin peptidomimetic DOTA-Gly-Ser-Cys(succinimidopropionyl-Glu-Ala-Tyr-Gly-Trp-Nle-Asp-Phe-NH$_2$)-Glu-Ala-Tyr-Gly-Trp-Nle-Asp-Phe-NH$_2$ (DOTA-MGD5) (Sosabowski J K et al., J Nucl Med 2009, 50: 2082-2089) or by the dual-modality fluorescent and radiolabelled ligand DOTA-Lys(IRDye-650)-PEG4-[D-Phe$^6$,Sta$^{13}$]-bombesin(6-14)NH$_2$ (HZ220) targeting the gastrin-releasing peptide receptor antagonist (Zhang H et al., J Nucl Med 2017, 58: 29-35). DOTA-MGD5 is a divalent MG analogue based on a maleimide-linker for which a high tumour uptake and low kidney retention has been shown in preclinical studies. The gastrin-releasing peptide receptor antagonist HZ220 targeting gastrin-releasing peptide (GRP) receptors is based on a bombesin analogue in which the two amines of a lysine are used to conjugate the chelator DOTA and the near-infrared fluorescent (NIRF) dye IRDye 650. For $^{68}$Ga-labelled HZ220 a high tumour-to-background contrast could be achieved for both PET and optical imaging. A linker can also be used to introduce a cleavable group into the peptide sequence, releasing a part of the peptide conjugate, such as a peptide fragment, a cytotoxic or a reporter group. Such an example is given by cathepsin B cleavage sites (Naqvi S A et al., Cancer Biother Radiopharm 2010, 25: 89-95; Albericio F and Kruger H G, Future Med Chem 2012, 4: 1527-1231). Also a combination of linkers, such as the combination of glucose and 4-aminobenzoic acid in the bombesin derivative $^{177}$Lu-DOTA-Lys(glucose)-4 aminobenzoic acid-BBS7-14 can be used (Lim J C et al, Nucl Med Biol 2015, 42:234-241).

As used herein, "pharmacokinetic modifier" means a chemical moiety that influences the pharmacokinetics of the peptidomimetic, such as the hydrophilicity, biodegradation, and clearance. For instance, the pharmacokinetic modifier may increase the half-life of the peptidomimetic in the blood stream.

The radiolabelled MG analogue DOTA-His-His-Glu-Aly-Tyr-Gly-Trp-Met-Asp-Phe-NH$_2$ (SEQ ID NO:17) (Mather S J et al., J Nucl Med 2007, 48: 615-622) is derived from MG11 and includes two His residues in the N-terminal part of the peptide. The radiolabeled MG analogues DOTA-DGln-DGln-DGln-DGln-DGln-DGln-Aly-Tyr-Gly-Trp-Met-Asp-Phe-NH$_2$, DOTA-DGln-DGln-DGln-Ala-Tyr-Gly-Trp-Met-Asp-Phe-NH$_2$, DOTA-DGln-DGlu-DGln-DGlu-DGln-DGlu-Ala-Tyr-Gly-Trp-Met-Asp-Phe-NH$_2$ and DOTA-DGlu-DGlu-DGlu-DGlu-DGlu-DGlu-Ala-Tyr-Gly-Trp-Met-Asp-Phe-NH$_2$ are derived from MG0 and include different numbers of DGln and DGlu residues in the N-terminal part of the peptide (Laverman P et al., Eur J Nucl Med Mol Imaging 2011, 38: 1410-1416). The design of these novel peptide derivatives was based on the knowledge that the high renal uptake of MG0 is caused by the anionic pentaglutamate sequence in the structure. By the introduction of positively charged residues and D-amino acid residues the kidney uptake could be reduced with a concomitant improved tumour-to-kidney ratio. To obtain a high tumour-to-background contrast in imaging a rapid clearance of the radioligand from the circulation is desirable. Also other spacers with different polarities, including PEG or D-amino acids such as D-Ser and D-Gln, have been studied as pharmacokinetic modifiers for MG analogues in the attempt to increase the stability and tumour-to-kidney ratio of the radioligands (Kolenc-Peitl P et al., J Med Chem 2011, 54: 2602-2609). By introducing hydrophilic and uncharged spacers of different lengths favourable effects on serum stability, kidney uptake and tumour-to-kidney ratio could be observed.

Linkage of the Reporter Group and Cytotoxic Group

The peptidomimetic of the present invention may comprise a reporter group or a cytotoxic group or multiple reporter groups or cytotoxic groups. In some embodiments the peptidomimetic may also comprise a reporter group and a cytotoxic group. In some embodiments the reporter group, the cytotoxic group, or both, can be directly linked to the amino acid polymer of the peptidomimetic, for example, through a covalent bond. In other embodiments the reporter group, the cytotoxic group, or both, can be indirectly linked to the amino acid polymer of the peptidomimetic.

If the reporter group, or the cytotoxic group, or both, are indirectly linked to the amino acid polymer of the peptidomimetic, they are linked to the amino acid polymer through a linker or pharmacokinetic modifier as defined above, or through a chelator or a prosthetic group. For instance, reporter groups that are fluorophores are preferably covalently linked to the amino acid polymer of the peptidomimetic, either directly or through a linker or spacer, such as polyethylenglycol. On the other hand, radionuclides, such as metal radionuclides, and metal ions are preferably linked to the peptidomimetic via a chelator. Radionuclides of halogens are preferably linked to the peptidomimetic via a prosthetic group or via a functional group of a side chain of an amino acid.

The reporter group or cytotoxic group can be directly or indirectly linked to the amino acid polymer of the peptidomimetic via the N-terminus, C-terminus or via an amino acid side chain, for example lysine or cysteine or via a functional group of a linker or pharmacokinetic modifier. Preferably, the reporter group or cytotoxic group is linked to the amino acid polymer of the peptidomimetic via the N-terminus. In preferred embodiments of the present invention, the reporter group or cytotoxic group is linked to the N-terminus of the peptide through a chelator or prosthetic group. In particular, in some embodiments, radionuclides are linked to the amino acid polymer of the peptidomimetic via the N-terminus of the peptide. A linker may be additionally used to connect the chelator or prosthetic group to the N-terminus or a side chain of an amino acid in the peptide sequence. The reporter group, for instance, the radionuclide can be coordinated by the chelator or introduced into the prosthetic group before or after conjugation with the peptide conjugate.

Chelator and Prosthetic Group

For the introduction of the reporter group or cytotoxic group the peptidomimetic can comprise a chelator or a prosthetic group. The chelator or prosthetic group can be conjugated to the amino acid polymer of the peptidomimetic at the N-terminus, the C-terminus or at any amino acid side chain or functional group present in a linker or pharmacokinetic modifier. Preferably, the chelator or prosthetic group is conjugated to the amino acid polymer of the peptidomimetic at the N-terminus.

The introduction of the reporter group or cytotoxic group into the chelator or prosthetic group can be performed before or after conjugation of the chelator or prosthetic group with the amino acid polymer of the peptidomimetic.

In some embodiments the chelator coordinates a metal, for example a metal radionuclide as mentioned herein, as a reporter group or a cytotoxic group or the prosthetic group comprises a halogen, for example a halogen radionuclide as mentioned herein, as a reporter group or a cytotoxic group.

The chelator may contain different donor groups for metal complexation such as oxygen, nitrogen, sulphur, (carboxyl, phosphonate, hydroxamate, amine, thiol, thiocarboxylate or derivatives thereof) and comprises acyclic and macrocyclic chelators such as polyaminopolycarboxylic ligands.

In some embodiments the chelator is selected from the group consisting of diethylenetriaminopentaacetic acid (DTPA), ethylenediaminetetraacetic acid (EDTA), 1,4,7-triazacyclononane-1,4,7-tris[methylene(2-carboxyethyl)] phosphinic acid (TRAP), 1,4,7,10-tetraazacyclododecane-1,4,7,10-tetraacetic acid (DOTA), 1,4,7-triazacyclononane-1,4,7-triacetic acid (NOTA), 1,4,7-triazacyclononane-1,4-diiacetic acid (NODA), 1,4,8,11-tetraazacyclotetradecane-1,4,8,11-tetraacetic acid (TETA) as well as derivatives thereof such as DOTA or NOTA functionalized with a glutaric acid arm (DOTAGA, NOTAGA). Other chelators are also contemplated in particular chelators for chelating radiometals.

Further chelators that are contemplated, for example for chelating $^{99m}$Tc, include, but are not limited to, diamidedithiols ($N_2S_2$), triamidethiols ($N_3S$), tetraamines ($N_4$) and hydrazinonicotinic acid (HYNIC). HYNIC is usually used in combination with co-ligands to complete the coordination sphere of the metal, which include and are not limited to ethylendiamine-N,N'-diacetic acid (EDDA) and tricine. In some embodiments, using the organometallic aqua ion $^{99m}$Tc(CO)$_3$(H$_2$O)$_3$, tricarbonyl complexes can be generated by exchanging water molecules with mono-, di- and tridentate chelators to form stable complexes including also the click-to-chelate methodology.

Further chelators, which are for example useful for labelling the peptidomimetics with $^{68}$Ga, include, but are not limited to N,N'-bis[2-hydroxy-5-(carboxyethyl)benzyl]ethylenediamine-N,N'-diacetic acid (HBED-CC), siderophore-based ligands such as desferrioxamine, hydroxypyridinone ligands such as deferiprone and tris(hydroxypyridinone) (THP), and derivatives thereof.

Preferred prosthetic groups of the present invention labelled with radionuclides of halogens such as iodine or fluorine, for example those mentioned herein. In some embodiments the prosthetic group will be selected from a group consisting of the Bolton-Hunter reagent, N-succinimidyl-5-(trialkylstannyl)-3-pyridinecarboxylates or N-succinimidyl-4-[$^{131}$I]iodobenzoate ([$^{131}$I]SIB) for radioiodination. In some embodiments the prosthetic group will be selected from a group comprising but not limited to 4-[$^{18}$F]fluorophenacyl bromide, N-succinimidyl-4-[$^{18}$F]fluorobenzoate ([$^{18}$F]SFB), N-succinimidyl-4-([$^{18}$F]fluoromethyl)benzoate, 4-[$^{18}$F]fluorobenzaldehyde, 6-[$^{18}$F]fluoronicotinic acid tetrafluorophenyl ester ([$^{18}$F]F-Py-TFP), silicon-containing building blocks such as N-Succinimidyl 3-(di-tert-butyl[$^{18}$F] fluorosilyl)benzoate ([$^{18}$F]SiFB), carbohydrate-based prosthetic groups, such as [$^{18}$F]fluoro-deoxyglucose, preferably 2-[$^{18}$F]fluoro-2-deoxyglucose ([$^{18}$F]FDG), and [$^{18}$F]fluoro-deoxymannose, preferably [$^{18}$F]2-fluoro-2-deoxymannose, or derivatives thereof, maleimide-based and heterocyclic methylsulfone-based $^{18}$F-synthons, $^{18}$F-labelled prosthetic groups such as $^{18}$F-azides or $^{18}$F-alkynes permitting labelling via click chemistry, $^{18}$F-labelled organotrifluoroborates and [$^{18}$F]fluoropyridines. In some embodiments a chelator-based labelling approach using aluminum-fluoride (Al$^{18}$F) is applied for radiofluorination.

Further Aspects and Embodiments of the Invention

The present invention also relates to a method of producing the present peptidomimetics as described herein. Production of the present peptidomimetics is possible by standard organic chemistry methods and solid phase peptide synthesis methods available to the person skilled in the art. The method at least comprises synthesizing the amino acid polymer of the peptidomimetic (Behrendt R et al., J Pept Sci 2016, 22: 4-27; Jones J, Amino Acid and Peptide Synthesis, Oxford University Press, New York 2002; Goodman M, Toniolo C, Moroder L, Felix A, Houben-Weyl Methods of Organic Chemistry, Synthesis of Peptides and Peptidomimetics, workbench edition set, Thieme Medical Publishers, 2004).

The present invention further relates to pharmaceutical and diagnostic compositions comprising the peptidomimetic described herein. Pharmaceutical compositions according to the present invention can be used in the treatment of CCK2R related diseases, such as diseases that are characterized by CCK2R expression or overexpression. In some embodiments the pharmaceutical compositions of the present invention can be used in the treatment of cancer, in particular such cancers that are characterized by expression of CCK2R. In some embodiments of the present invention the pharmaceutical compositions of the present invention can be used to deliver a cytotoxic group, such as a chemotherapeutic agent or a radionuclide to CCK2R expressing tumour cells. Thus, pharmaceutical compositions of the present invention can be used for targeted cancer therapy.

The present invention also relates to a kit comprising one or more components of the present invention, for instance, the pharmaceutical or diagnostic composition according to the present invention or the peptidomimetic according to the present invention. The kit may further comprise an information leaflet that provides explanations how to prepare or use the peptidomimetic, pharmaceutical composition or diagnostic composition of the present invention. In one embodiment, the kit comprises the pharmaceutical or diagnostic composition of the present invention ready for use. In a further embodiment, the kit comprises two or more compositions that are sufficient to prepare the pharmaceutical or diagnostic composition, ready for use. For instance, in one embodiment, the kit may comprise a first composition comprising a peptidomimetic that comprises a chelator, and a second composition comprising a reporter or cytotoxic group. To prepare the final diagnostic or therapeutic composition, the skilled person would follow the information leaflet provided in the kit and combine the first and second composition to generate a ready to use diagnostic or therapeutic composition.

Diagnostic compositions of the present invention can be used for diagnostic purposes. Diagnostic compositions of the present invention can be administered to the patient as part of the diagnostic process, for example, to allow imaging of CCK2R expressing cells or tissues, for example CCK2R expressing tumour cells. The diagnostic composition of the present invention can be used in methods of imaging, such as methods of imaging according to the present invention, for example methods of imaging tumour cells.

The present invention also relates to a use of the peptidomimetic of the present invention described herein for delivering a reporter group or a cytotoxic group as described herein to a cell. Preferably, the reporter group or cytotoxic group is delivered to a cell that expresses CCK2R, for example a cancer cell expressing CCK2R. The use of the present peptidomimetic can be in vivo or in vitro. For example, the peptidomimetic of the present invention can be used to deliver a reporter group or a cytotoxic group to a human or animal, for example a mammal, such as mouse, rat, rabbit, hamster or other mammals. In some embodiments of the present invention the peptidomimetic can be used to deliver a reporter group or a cytotoxic group to cells ex vivo, for example, immortalized or primary cell lines that are cultured in cell culture.

The present invention also relates to a method of imaging cells as described herein. The method of imaging cells described herein makes use of the peptidomimetic described herein. In some embodiments of the present invention, the method of imaging cells makes use of a non-therapeutic peptidomimetic as described herein. The present method of imaging cells may involve or can be based on established methods of imaging, such as computer tomography (CT), magnetic resonance imaging (MRI), scintigraphy, SPECT, PET, or other similar techniques. Based on the individual method of imaging that is used, the skilled person will select the proper reporter group. The present method of imaging cells can be carried out in vivo or in vitro. In some embodiments of the present invention contacting a cell with the peptidomimetic of the present invention involves administering the peptidomimetic described herein to a patient, for example a patient that suffers from cancer, for example a cancer that involves the expression of CCK2R. In some preferred embodiments the cell is a tumour cell. Thus, in some preferred embodiments a tumour cell is contacted with the peptidomimetic. In some preferred embodiments, the tumour cell expresses CCK2R.

In some embodiments, the present invention also relates to a method of treating a patient that suffers from a disease that involves the expression of CCK2R, for example a cancer that is characterized by the expression of CCK2R in the tumour cells. Such a method of treating a patient involves the administration of the peptidomimetic of the present invention to the patient.

In some embodiments, the present invention relates to the peptidomimetic described herein for use in therapy. In preferred embodiments of the present invention the peptidomimetic is for use in the treatment of cancer. Preferably, the cancer is a cancer that expresses CCK2R on the surface of tumour cells.

The peptidomimetic of the present invention is useful for the diagnostic workup and treatment of various types of cancer, for example: thyroid cancer such as medullary thyroid carcinomas (MTC), lung cancers such as small cell lung cancer (SCLC), gastrointestinal stromal tumours, tumours of the nervous system such as astrocytomas and meningiomas, stromal ovarian cancers, gastrointestinal cancers, neuroendocrine tumours, gastroenteropancreatic tumours, neuroblastomas, tumours of the reproductive system such as breast carcinomas, endometrial carcinomas, ovarian cancers and prostate carcinomas, insulinomas, vipomas, bronchial and ileal carcinoids, leiomyosarcomas, leiomyomas and granulosa cell tumours. In some preferred embodiments the above mentioned types of cancer express CCK2R.

EXAMPLES

Example 1: Synthesis of the Peptidomimetics of the Present Invention

The synthesis of the peptidomimetics of the present invention was performed using standard 9-fluorenylmethoxycarbonyl (Fmoc) chemistry.

The peptidomimetics were assembled on a Rink Amide MBHA resin (Novabiochem, Hohenbrunn, Germany) in N-methyl-2-pyrrolidone (NMP) using an excess of Fmoc-protected amino acid, 1-Hydroxy-7-azabenzotriazole (HOAt), and (2-(7-Aza-1H-benzotriazole-1-yl)-1,1,3,3-tetramethyluronium hexafluorophosphate (HATU) in alkaline medium. The reactive side chains of the amino acids were masked with appropriate protection groups. After assembling the desired amino acid sequence, coupling of Boc protected DOTA or HYNIC was performed followed by cleavage of the peptidomimetic from the resin with concomitant removal of acid-labile protecting groups. After HPLC purification and lyophilization the peptidomimetics were obtained in >20% yield with a chemical purity ≥95% as confirmed by RP-HPLC and MALDI-TOF MS. Radiolabelling of the inventive peptidomimitics with different radiometals was performed using standard radiolabelling protocols by dissolving the peptide in aqueous solution such as 25-50% ethanol and mixing the solution with an acidic solution such as hydrochloric acid containing the radiometal and a solution such as sodium acetate solution or ascorbic acid solution for pH adjustment and incubating the mixture at high temperature (90-95° C.) for approximately 30 min. Radiolabelling with the different radiometals resulted in high labelling yields and radiochemical purity. HPLC analysis of the peptidomimetics and of the radiolabelled derivatives was performed on a Dionex chromatography system consisting of a Dionex UltiMate 3000 Pump (Dionex, Gemering, Deutschland), UV detection at 280 nm (UltiMate 3000 variable UV-detector) and radiodetection (Gabi Star, Raytest, Straubenhardt, Germany) and using a Phenomenex Jupiter 4μ Proteo 90A 250×4.6 (C12) column and a flow rate of 1 mL/min together with a gradient system of water containing 0.1% TFA (solvent A) and acetonitrile containing 0.1% TFA (solvent B): 0-3 min 10% B, 3-18 min 10-55% B, 18-20 min 80% B, 20-21 min 10% B, 21-25 min 10%.

The following peptidomimetics (Table 4) were synthesized according to the above method:

TABLE 4

| Name | Structure |
| --- | --- |
| DOTA-MGS5 | DOTA-DGlu-Ala-Tyr-Gly-Trp-(N-Me)Nle-Asp-1Nal-NH$_2$ |
| HYNIC-MGS5 | HYNIC-DGlu-Ala-Tyr-Gly-Trp-(N-Me)Nle-Asp-1Nal-NH$_2$ |
| DOTA-MGS5-2 | DOTA-DGlu-Ala-Tyr-Gly-Trp-(N-Me)Nle-Asp-2Nal-NH$_2$ |
| DOTA-MGS8 | DOTA-DGlu-Pro-Tyr-Gly-Trp-(N-Me)Nle-Asp-1Nal-NH$_2$ |
| DOTA-MGS9 | DOTA-DLys-Ala-Tyr-Gly-Trp-(N-Me)Nle-Asp-1Nal-NH$_2$ |
| DOTA-MGS10 | DOTA-DGlu-Tyr-Pro-Gly-Trp-(N-Me)Nle-Asp-1Nal-NH$_2$ |
| DOTA-MGS11 | DOTA-DGlu-Ala-Tyr-Gly-Trp-(N-Me)Nle-Asp-(N-Me)1Nal-NH$_2$ |
| HYNIC-MGS11 | HYNIC-DGlu-Ala-Tyr-Gly-Trp-(N-Me)Nle-Asp-(N-Me)1Nal-NH$_2$ |
| DOTA-MGS12 | DOTA-DGlu-Ala-Tyr-Pro-Trp-(N-Me)Nle-Asp-1Nal-NH$_2$ |
| DOTA-MGS16 | DOTA-DGlu-Ala-Tyr-Gly-Trp-(N-Me)Nle-Asp-Phe-NH$_2$ |

Example 2: Peptidomimetics of the Present Invention have Increased Stability in Human Serum In Vitro To characterise the radiolabelled peptidomimetics in vitro, the stability in human serum was studied. The peptidomimetics labelled with $^{111}$In were incubated in fresh human serum at a concentration of 500-2000 pmol/mL at 37° C. for up to 24 h and the degradation was assessed by radio-HPLC. For this purpose human serum samples were precipitated with ACN, centrifuged at 2000 g for 2 min and diluted with water (1:1/v:v) prior to HPLC analysis on a Dionex chromatography system including radiodetection and UV detection equipped with a Phenomenex Jupiter Proteo C12 column (90 Å, 4 µm, 250×4.6 mm) column or a Bischoff Chromatography Nucleosil C18 column (120 Å, 5 µm, 250×4.6 mm) using different water/acetonitrile/0.1% TFA gradient systems. As shown in FIG. 1, the stability of the radiolabelled peptidomimetics in human serum was considerably increased when compared with $^{111}$In-labelled DOTA-MG11 and $^{111}$In-DOTA-MGS1, showing 16.1% (n=2) and 60.1% (n=1) intact radiolabelled peptidomimetic after 24 h incubation, respectively. For the same time point $^{111}$In-DOTA-MGS5, $^{111}$In-DOTA-MGS5-2, $^{111}$In-DOTA-MGS8, $^{111}$In-DOTA-MGS9 and $^{111}$In-DOTA-MGS10 showed values >94% and therefore displayed a much higher stability against enzymatic degradation. $^{111}$In-DOTA-MGS11 and $^{111}$In-DOTA-MGS12 also showed a >94% intact radiopeptide in human serum. This stabilization is achieved by applying at least two substitutions in the C-terminal receptor-specific sequence of MG, preferably combined with additional N-terminal substitutions. We have additionally studied $^{111}$In-DOTA-MGS16 with single substitution of Met with (N-Me)Nle finding a partial stabilization (53.1% intact radiopeptide, n=2). This confirms that a single substitution with, for example, (N-Me)Nle or 1 Nal does not completely protect the peptidomimetic against degradation, only a combination of substitutions in different positions, as according to the present invention, allows completely stabilizing the peptidomimetic.

Example 3: Peptidomimetics of the Present Invention Bind to Serum Proteins

Additionally, protein binding to serum proteins was investigated. For this purpose the $^{111}$In-labelled peptidomimetics were incubated in duplicates in fresh human serum at 37° C. (500 pmol/mL) and analyzed after 4 and 24 h by Sephadex G-50 size-exclusion chromatography (GE Healthcare Illustra, Little Chalfont, UK). The percentage of protein binding was determined by measuring the column and the eluate in a 2480 Wizard 2 automatic gamma-counter (Perkin Elmer Life Sciences and Analytical Sciences, Turku, F). The results are summarized in Table 5.

TABLE 5

| Peptidomimetic | Percentage of radioligand bound to serum proteins after 4 h incubation | Percentage of radioligand bound to serum proteins after 24 h incubation |
| --- | --- | --- |
| $^{111}$In-DOTA-MG 11 | 10.1 ± 2.7% | 6.25 ± 1.7% |
| $^{111}$In-DOTA-MGS1 | 20.0 ± 1.8% | 28.8 ± 3.5% |
| $^{111}$In-DOTA-MGS4 | 8.9 ± 4.5% | 11.9 ± 4.7% |
| $^{111}$In-DOTA-MGS5 | 41.0 ± 0.2% | 44.3 ± 0.3% |
| $^{111}$In-DOTA-MGS5-2 | 31.7 ± 0.7% | 34.6 ± 0.3% |
| $^{111}$In-DOTA-MGS8 | 44.5 ± 1.8% | 52.8 ± 0.1% |
| $^{111}$In-DOTA-MGS9 | 26.6 ± 0.8% | 27.8 ± 0.4% |
| $^{111}$In-DOTA-MGS10 | 56.7 ± 0.1% | 53.4 ± 0.2% |
| $^{111}$In-DOTA-MGS11 | 31.9 ± 0.3% | 39.8 ± 4.2% |
| $^{111}$In-DOTA-MGS12 | 41.2 ± 0.04% | 45.9 ± 0.5% |

Protein binding of $^{111}$In-labelled peptidomimetics determined after 4 and 24 h incubation in human serum in comparison with $^{111}$In-DOTA-MG11, $^{111}$In-DOTA-MGS1 and $^{111}$In-DOTA-MGS4 (expressed as percentage of radioligand bound to serum proteins)

When compared with $^{111}$In-DOTA-MG11 showing a protein binding of <10% after 24 h incubation, $^{111}$In-DOTA-MGS4 showed a similar protein binding (~12%). The radiolabelled peptidomimetics of the present invention showed a higher protein binding, as indicated in Table 5. $^{111}$In-DOTA-MGS5-2, $^{111}$In-DOTA-MGS9 and $^{111}$In-DOTA-MGS11 showed an intermediate protein binding of ~30%. With four peptidomimetics high protein binding was observed with values >40% for $^{111}$In-DOTA-MGS5 and $^{111}$In-DOTA-MGS12, and >50% for $^{111}$In-DOTA-MGS8 and $^{111}$In-DOTA-MGS10 after 24 h incubation.

Example 4: Peptidomimetics of the Present Invention have High Affinity for CCK2R Affinity for CCK2R was studied in A431 human epidermoid carcinoma cells stably transfected with the plasmid pCR3.1 containing the full coding sequence for the human CCK2R (A431-CCK2R) kindly provided by Dr. Luigi Aloj (Aloj L et al., J Nucl Med 2004, 45: 485-494). The binding affinity was tested in a competition assay against [$^{125}$I]Tyr$^{12}$-gastrind in comparison with pentagastrin (Boc-β-Ala-Trp-Met-Asp-Phe-NH$_2$; SEQ ID NO:18), DOTA-MG11, and PP-F11, a peptide analogue derived from MG0 by substitution of the penta-Glu sequence with five D-glutamic acid residues, as well as DOTA-MGS1 and DOTA-MGS4. Radioiodination of gastrin-1 was carried out using the chloramine-T method. Non-carrier-added [$^{125}$I-Tyr$^{12}$]gastrind was obtained by HPLC purification and stored in aliquots at −20° C. Binding assays were carried out in 96-well filter plates (MultiScreen$_{HTS}$-FB, Merck Group, Darmstadt, Germany) pretreated with 10 mM TRIS/139 mM NaCl pH 7.4 (2×250 μl). For the assay a number of 200,000-400,000 A431-CCK2R cells per well was prepared in 35 mM HEPES buffer pH 7.4 containing 10 mM MgCl$_2$, 14 μM bacitracin and 0.5% BSA (a hypotonic solution disturbing the integrity of the cell membranes). The cells were incubated in triplicates with increasing concentrations of the peptidomimetics (0.0003 to 10,000 nM, for example 0.001 to 1000 nM) and [$^{125}$I-Tyr$^{12}$]gastrin-I (20,000-60,000 cpm) for 1 h at RT. Incubation was interrupted by filtration of the medium and rapid rinsing with ice-cold 10 mM TRIS/139 mM NaCl pH 7.4 (2×200 μl) and the filters were counted in the gamma-counter. Half maximal inhibitory concentration (IC50) values were calculated following nonlinear regression with Origin software (Microcal Origin 6.1, Northampton, MA) and a representative assay was chosen for comparison. As shown in Table 6 a high binding affinity for the CCK2R with IC50 values in the low nanomolar range could be confirmed for all tested peptidomimetics.

TABLE 6

| Tested CCK2R ligand | IC50 [nM] |
| --- | --- |
| pentagastrin | 0.9 ± 0.3 |
| DOTA-MG11 | 0.9 ± 0.5 |
| PP-F11 | 0.4 ± 0.1 |
| DOTA-MGS1 | 1.9 ± 0.2 |
| DOTA-MGS4 | 1.2 ± 0.2 |
| DOTA-MGS5 | 0.4 ± 0.2 |
| HYNIC-MGS5 | 6.0 ± 1.5 |
| DOTA-MGS5-2 | 1.6 ± 0.4 |
| DOTA-MGS8 | 1.6 ± 0.2 |
| DOTA-MGS9 | 1.8 ± 0.4 |
| DOTA-MGS10 | 0.9 ± 0.2 |

Receptor binding of the inventive CCK2R targeting peptidomimetics in comparison with pentagastrin, DOTA-MG11, DOTA-MGS1 and DOTA-MGS4 on A431-CCK2R cells as analyzed by displacement with [$^{125}$I]Tyr$^{12}$-gastrind-I Example 5: Peptidomimetics of the Present Invention Show Improved Cellular Internalization These studies were carried out according to a previously published protocol (von Guggenberg E et al., Bioconjug Chem 2004, 15: 864-871) using 1.0 million of A431-CCK2R cells as well as the same cell line transfected with the empty vector alone (A431-mock) as a control. DMEM supplemented by 1% (v/v) fetal bovine serum was used as internalization medium and the non-specific cell uptake was studied in A431-mock cells instead of performing blocking studies. The cells were incubated in triplicates with 10,000-500,000 cpm, for example 10,000-30,000 cpm of radiolabelled peptidomimetic (corresponding to a final concentration of 0.4 nM and ~600 fmol of total peptidomimetic in the assay) and incubated at 37° C. for 2 h. The internalized fraction in A431-CCK2R and A431-mock cells was expressed in relation to the total activity added (% of total).

For each radiolabelled peptidomimetic the mean value of one representative assay performed in triplicates is represented. For $^{111}$In-DOTA-MGS1 and $^{111}$In-DOTA-MGS4 the mean value of the cell uptake obtained from two independent assays was considered.

Figure 2:
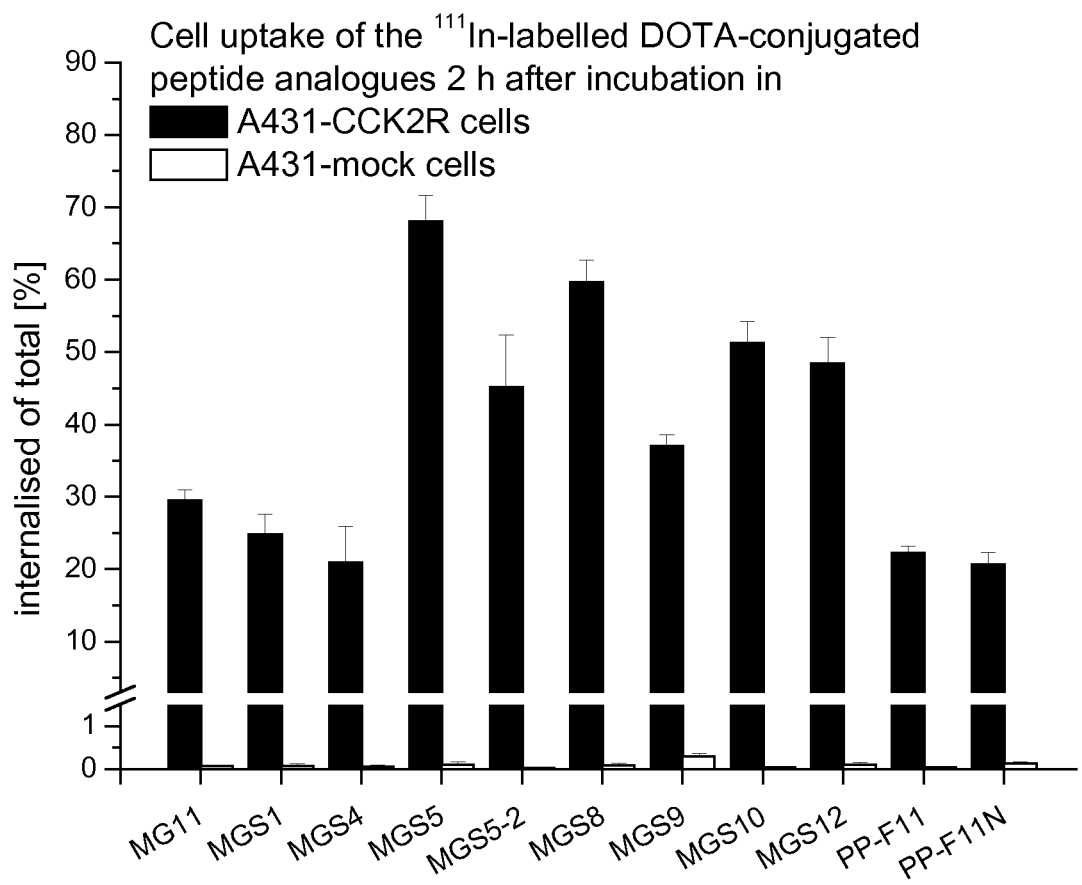
FIG. 2 the cell internalization of the $^{111}$In-labelled peptidomimetics of the present invention in comparison with $^{111}$In-DOTA-MG11 $^{111}$In-PP-F11 $^{111}$In-PP-F11N, $^{111}$In-DOTA-MGS1 and $^{111}$In-DOTA-MGS4 after 2 h incubation on A431-CCK2R and A431-mock cells.

The cellular internalization of different radiolabelled peptidomimetics of the present invention was compared to PP-F11 and PP-F11N. These two peptide derivatives are derived from MG0 by substitution of the penta-Glu sequence with five D-glutamic acid residues and additional substitution of Met with Nle in PP-F11N. In comparison with PP-F11 and PP-F11N labelled with $^{111}$In and $^{177}$Lu all radiolabelled peptidomimetics of the present invention show an increased cellular internalization. As shown in FIG. 2 for the $^{111}$In-labelled peptidomimetics, the internalized radioligand fraction after 2 h incubation resulted to be highest for $^{111}$In-DOTA-MGS5, $^{111}$In-DOTA-MGS8, $^{111}$In-DOTA-MGS10 and $^{111}$In-DOTA-MGS12 with values of 47-68%. These peptidomimetics also showed the highest levels of protein binding. Peptidomimetics with intermediate protein binding showed a somewhat lower cell uptake with values of 37% for $^{111}$In-DOTA-MGS9 and 45% for $^{111}$In-DOTA-MG5-2. The cell uptake of all radiolabelled peptidomimetics was considerable higher in comparison with the reference compounds $^{111}$In-PP-F11 and $^{111}$In-PP-F11N, showing a cellular internalization below 24%, with the control peptide $^{111}$In-DOTA-MG11 (29%), as well as $^{111}$In-DOTA-MGS1 and $^{111}$In-DOTA-MGS4 (21-25%), two peptide derivatives previously studied (Klingler M et al., Eur J Nucl Med Mol Imaging 2017, 44: S228). The negligible uptake in A431-mock cells without CCK2R expression (<1%) confirms the receptor-specific cell uptake.

Figure 3:
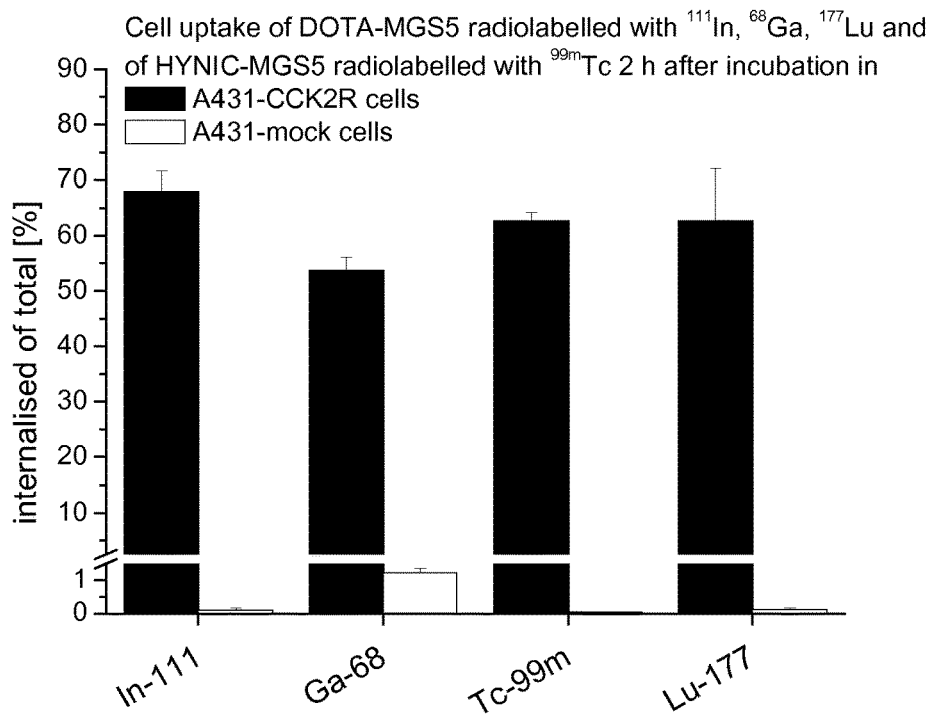
FIG. 3 the cell internalization of the peptidomimetics of the present invention after 2 h incubation on A431-CCK2R and A431-mock cells: A) DOTA-MGS5 radiolabelled with $^{111}$In, $^{68}$Ga and $^{177}$Lu as well as HYNIC-MGS5 labelled with $^{99m}$Tc and B) DOTA-MGS1 PP-F11 and PP-F11N radiolabelled with $^{177}$Lu and C) DOTA-MGS12 radiolabelled with $^{68}$Ga.
Figure 3:
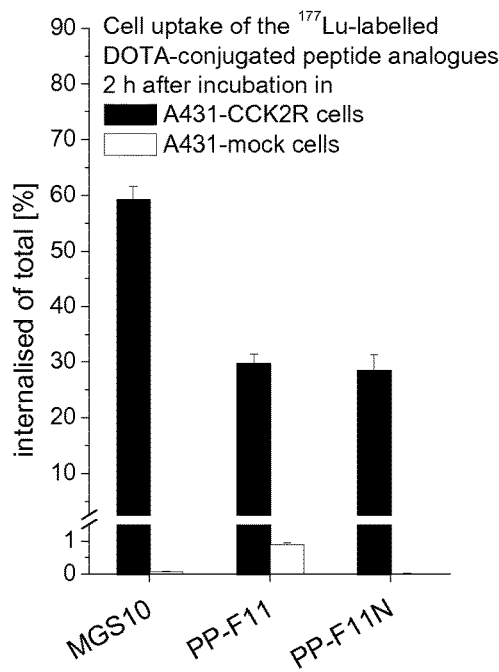
Figure 3:
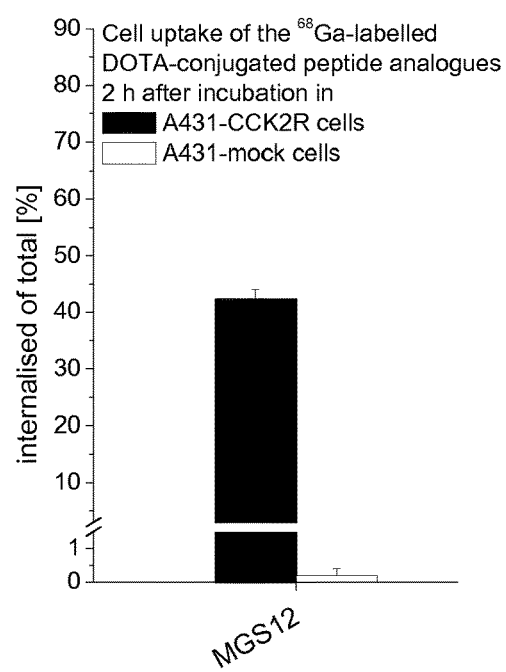

Further cell uptake studies were performed with different DOTA and HYNIC conjugated peptidomimetics of the present invention to confirm the surprisingly high cell uptake also for radiolabelling with other radiometals. As shown in FIG. 3, also for the peptidomimetics radiolabelled with either $^{111}$In, $^{177}$Lu, $^{68}$Ga or $^{99m}$Tc, a very high cell uptake was observed. Values of 68% for $^{111}$In-DOTA-MGS5, 54% for $^{68}$Ga-DOTA-MGS5 and 63% for $^{99m}$Tc-HYNIC-MGS5 and $^{177}$Lu-DOTA-MGS5 were measured (FIG. 3A). $^{177}$Lu-DOTA-MGS10 also showed a cellular internalization >50%, whereas a much lower uptake (<30%) was found for $^{177}$Lu-PP-F11 and $^{177}$Lu-PP-F11N (FIG. 3B). $^{68}$Ga-DOTA-MGS12 showed a cellular internalization of ~40% (FIG. 3C). The cell uptake in A431-mock cells was below 1.5%.

Figure 4:
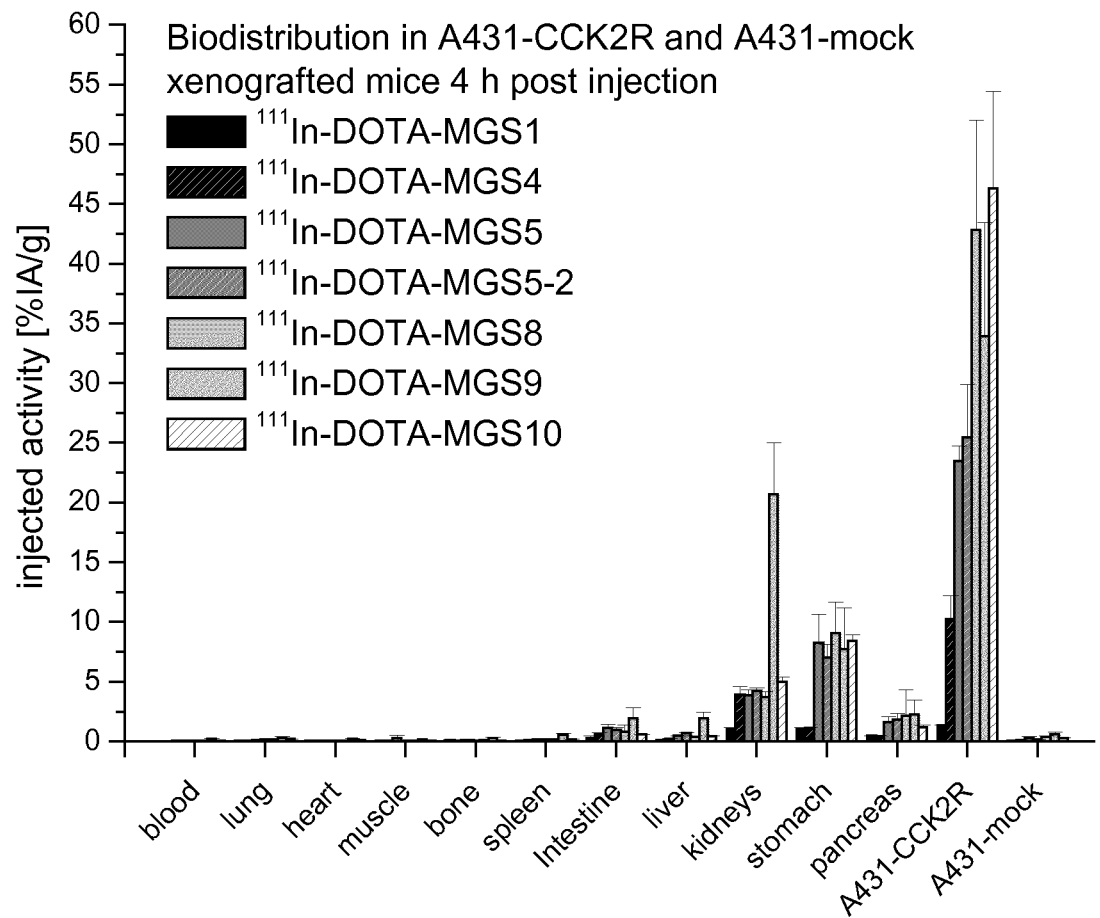
FIG. 4 the biodistribution in A431-CCK2R and A431-mock tumour-xenograft bearing nude mice of selected $^{111}$In-labelled peptidomimetics of the present invention in comparison with $^{111}$In-DOTA-MGS1 and $^{111}$In-DOTA-MGS4 at 4 h p.i. Values are expressed as percentage of injected activity per gram (% IA/g; mean±SD, n=4; $^{111}$In-DOTA-MGS1 and $^{111}$In-DOTA-MGS4 n=3).
Figure 5:
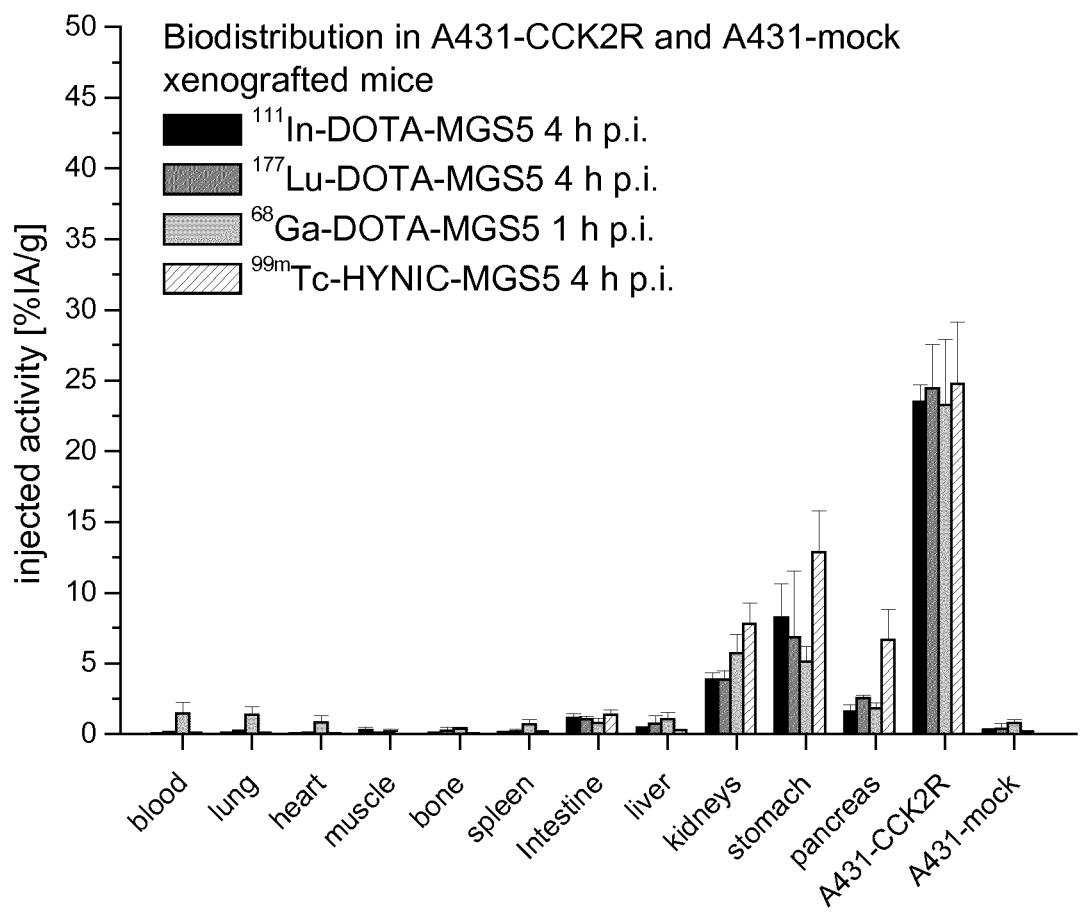
FIG. 5 the biodistribution in A431-CCK2R and A431-mock tumour-xenograft bearing nude mice of the peptidomimetic DOTA-MGS5 radiolabelled with $^{111}$In, $^{68}$Ga and $^{177}$Lu as well as HYNIC-MGS5 labelled with $^{99m}$Tc for different time points of 1 h or 4 h p.i. Values are expressed as % IA/g (mean±SD, n=4).

Example 6: Peptidomimetics of the Present Invention Show Improved Biodistribution In Vivo Biodistribution studies evaluating the tumour uptake of the radiolabelled inventive CCK2R targeting peptide analogues were performed in 7-week-old female athymic BALB/c nude mice (Charles River, Sulzfeld, Germany). All animal experiments were conducted in compliance with the Austrian animal protection laws and with the approval of the Austrian Ministry of Science. For the induction of tumour xenografts, A431-CCK2R and A431-mock cells were injected subcutaneously in the right and left flank respectively (2 million cells in 200 μl). When tumours had reached a size of approximately 0.2 ml biodistribution studies were carried out. Groups of 4 mice were injected intravenously via a lateral tail vein with the peptidomimetics of the present invention, labelled with $^{111}$In (approximately 0.2 MBq and 0.02 nmol peptidomimetic), with $^{68}$Ga (approximately 0.8 MBq and 0.02-0.03 nmol peptidomimetic), with $^{177}$Lu (approximately 0.5 MBq and 0.02 nmol peptidomimetic) or with $^{99m}$Tc (approximately 0.3 MBq and 0.02 nmol peptidomimetic). After a time period of 1 or 4 h post-injection (p.i.) the animals were sacrificed by cervical dislocation, tumours and other tissues (blood, lung, heart, muscle, bone, spleen, intestine, liver, kidneys, stomach, pancreas) were removed, weighed, and their radioactivity measured in the gamma counter. Results were expressed as percentage of injected activity per gram tissue (% IA/g) and tumour to organ activity ratios were calculated from the activity measured in the dissected tissues. In FIG. 4 the results of the biodistribution studies at 4 h p.i. are summarized for the $^{111}$In-labelled peptidomimetics of the present invention in comparison with $^{111}$In-DOTA-MGS1 and $^{111}$In-DOTA-MGS4 (Klingler M et al., Eur J Nucl Med Mol Imaging 2017, 44: S228). In FIG. 5 the results for the model peptidomimetics of the present invention, DOTA-MGS5 and HYNIC-MGS5, radiolabelled with different radiometals are shown for different time points of 1 or 4 h p.i. An overall highly improved biodistribution profile with fast blood clearance, predominant renal excretion and low unspecific uptake in most tissues and low kidney retention was observed for all radioligands. The different $^{111}$In-labelled peptidomimetics showed a higher uptake in CCK2R expressing tissues, stomach (~8% IA/g) and pancreas (~2% IA/g). $^{111}$In-DOTA-MGS9 showed a somewhat higher uptake in intestine and liver (~2% IA/g) and especially in kidneys (~20% IA/g). Given the crucial importance of the C-terminal Trp-Met-Asp-Phe-NH$_2$ (SEQ ID NO:18) tetrapeptide as principal pharmacophore for the CCK2R mediated actions (Stone S R et al., Peptides 2007, 28: 2211-2222) it was very surprising that the peptidomimetics of the present invention with two substitutions in this particular amino acid sequence showed highly specific tumour targeting in vivo in A431-CCK2R tumour xenografts. All peptidomimetics of the present invention showed a 2-40-fold, for example a 2.3 to 35.6-fold higher tumour uptake in comparison with $^{111}$In-DOTA-MGS1 (1.3±0.1% IA/g) and $^{111}$In-DOTA-MGS4 (10.2±2.0% IA/g) (Klingler M et al., Eur J Nucl Med Mol Imaging 2017, 44: S228). $^{111}$In-DOTA-MGS8 and $^{111}$In-DOTA-MGS10 with values of 42.8±2.3% IA/g and 46.3±8.2% IA/g at 4 h p.i., respectively, showed the highest tumour uptake. Also with $^{111}$In-DOTA-MGS9 a high tumour uptake was observed (33.9±9.5% IA/g) which was however accompanied by a higher kidney uptake (20.7±4.4% IA/g). $^{111}$In-DOTA-MGS5 and $^{111}$In-DOTA-MGS5-2 showed a tumour uptake of 23.5±1.3% IA/g and 25.5±4.5% IA/g, respectively. The uptake in A431-mock tumour xenografts with values <1% IA/g was very low confirming the high receptor-specific tumour uptake. Without being bound by theory, it is believed that higher stability, higher protein binding and improved cellular internalization also resulted in higher tumour uptake in vivo. A combination of high stability and increased protein binding in vivo seems therefore to result in an optimal protection of the radioligand against enzymatic degradation in blood allowing reaching an extremely high tumour uptake. This impressively high tumour uptake could be confirmed also for radiolabelling with different radioisotopes using DOTA-MGS5 and HYNIC-MGS5 as model peptidomimetics. $^{177}$Lu-DOTA-MGS5 (24.5±3.1% IA/g), $^{68}$Ga-DOTA-MGS5 (23.3±4.7% A/g) and $^{99m}$Tc-HYNIC-MGS5 (24.8±4.4% IA/g) showed a tumour uptake comparable to $^{111}$In-DOTA-MGS5 (23.5±1.3% IA/g). $^{68}$Ga-DOTA-MGS5 showed a somewhat higher unspecific tissue uptake in blood, lung and heart (1-2% IA/g), whereas the kidney uptake (4-6% IA/g) and the uptake in CCK2R expressing organs stomach (5-8% IA/g) and pancreas (2-3% IA/g) of DOTA-MGS5 labelled with Lu-177, Ga-68 and In-111 was comparable. $^{99m}$Tc-HYNIC-MGS5 showed the highest kidney uptake (8% IA/g) from all radioisotopes and a trend towards a higher uptake in stomach (13% IA/g) and pancreas (7% IA/g). In the A431-mock tumour xenografts a very low uptake <1% ID/g was observed for all radioligands, confirming the receptor specific uptake in the A431-CCK2R tumour xenografts.

The exceptional combination of low uptake in blood and normal tissue combined with very high tumour uptake and tumour retention over time resulted in very favourable tumour to organ activity ratios, especially for the peptidomimetics DOTA-MGS5, DOTA-MGS5-2, DOTA-MGS8 and DOTA-MGS10. High tumour-to-kidney ratios in the order of $^{111}$In-DOTA-MGS8 (11.6±3.0) >$^{111}$In-DOTA-MGS10 (9.3±2.0) >$^{111}$In-DOTA-MGS5 (6.4±0.6) >$^{111}$In-DOTA-MGS5-2 (6.0±0.9) were observed.

When comparing the tumour-to-kidney ratio of the model peptidomimetic MGS5 radiolabelled with different radioisotopes a tumour-to-kidney ratio in the order of $^{177}$Lu-DOTA-MGS5 (6.5±1.6) >$^{111}$In-DOTA-MGS5 (6.4±0.6) >$^{68}$Ga-DOTA-MGS5 (4.1±0.3) >$^{99m}$Tc-HYNIC-MGS5 (3.3±1.1) was reached. These impressing biodistribution properties remain unmatched in the literature. So far, similar improvements in the targeting profile of CCK2R targeting peptides have been achieved only by the co-administration of an enzyme inhibitor (Kaloudi A et al., Q J Nucl Med Mol Imaging 2015, 59: 287-302; Nock B A et al., J Nucl Med 2014, 55: 121-127). No similar report exists on a comparable improvement in tumour targeting by single injection of a radiolabelled CCK2R targeting peptide analogue alone. The peptidomimetics of the present invention therefore display outstanding properties. When comparing different $^{111}$In-labelled peptide analogues in the same tumour model $^{111}$In-DOTA-MG0 showed a tumour uptake of 9.9±2.0% ID/g and $^{111}$In-DOTA-MG11 of 3.04±1.30% ID/g (Laverman Petal., Eur J Nucl Med Mol Imaging 2011, 38: 1410-1416). In the series of radioligands studied $^{111}$In-PP-F11, a MG analogue with six D-Glu residues, showed the most favourable tumour retention (6.30±2.75% ID/g at 4 h p.i.) combined with a tumour-to-kidney ratio of 1.2±0.5. A similar tumour uptake has been reported also for $^{177}$Lu-PP-F11 (6.70±0.60% IA/g) and $^{177}$Lu-PP-F11N (6.90±0.80% IA/g) (Sauter A W et al., Eur J Nucl Med Mol Imaging 2016, 43: S238-S239).

The peptidomimetics of the present invention, in comparison, show a highly improved tumour uptake and tumour-to-kidney ratio, combining the positive features of MG0 (high tumour uptake) and MG11 (low kidney retention) and show a very favourable tumour to kidney ratio.

Example 7: Peptidomimetics of the Present Invention have Increased Stability In Vivo To further characterise the stability of the radiolabelled peptidomimetics in vivo, metabolic studies were carried out in 5-6-week-old female BALB/c mice (Charles River, Sulzfeld, Germany) injected intravenously with the $^{111}$In- and $^{111}$Lu-labelled peptidomimetics. All animal experiments were conducted in compliance with the Austrian animal protection laws and with the approval of the Austrian Ministry of Science. To allow monitoring of the metabolites by radio-HPLC, mice were injected with a higher amount of radioactivity (5-15 MBq $^{111}$In and 20-40 MBq $^{177}$Lu, corresponding to 1-2 nmol total peptide) through a lateral tail vein and euthanized by cervical dislocation 10 or 30 min post injection (p.i.). A sample of blood was collected and the degradation was assessed by radio-HPLC. For this purpose blood samples were precipitated with ACN, centrifuged at 2000 g for 2 min and diluted with water (1:1/v:v) prior to HPLC analysis using a Dionex chromatography system including radiodetection and UV detection equipped with a Phenomenex Jupiter Proteo C12 column (90 Å, 4 μm, 250×4.6 mm) column or a Bischoff Chromatography Nucleosil C18 column (120 Å, 5 μm, 250×4.6 mm) using different water/acetonitrile/0.1% TFA gradient systems.

Figure 6:
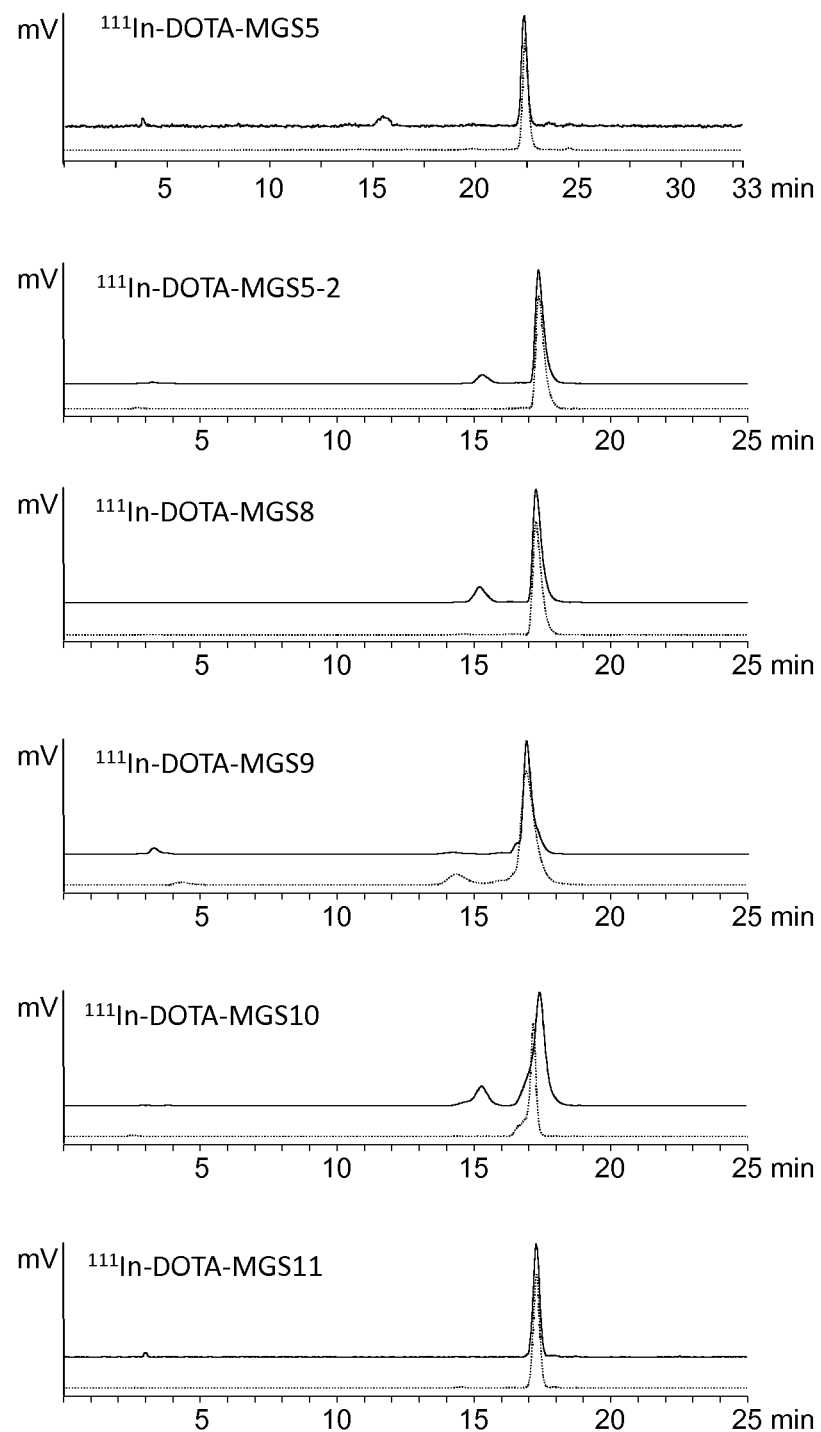
FIG. 6 the stability against enzymatic degradation in vivo as analyzed by radio-HPLC of a blood sample taken from BALB/c mice after intravenous injection of A) the $^{111}$In-labelled peptidomimetics of the present invention at 10 min p.i. and B) exemplary $^{177}$Lu-labelled peptidomimetics of the present invention in comparison with $^{177}$Lu-PP-F11 and $^{177}$Lu-PP-F11N at 30 min p.i.: radiochemical purity after radiolabelling (dotted line), radio-HPLC of the blood sample (solid line).
Figure 6:
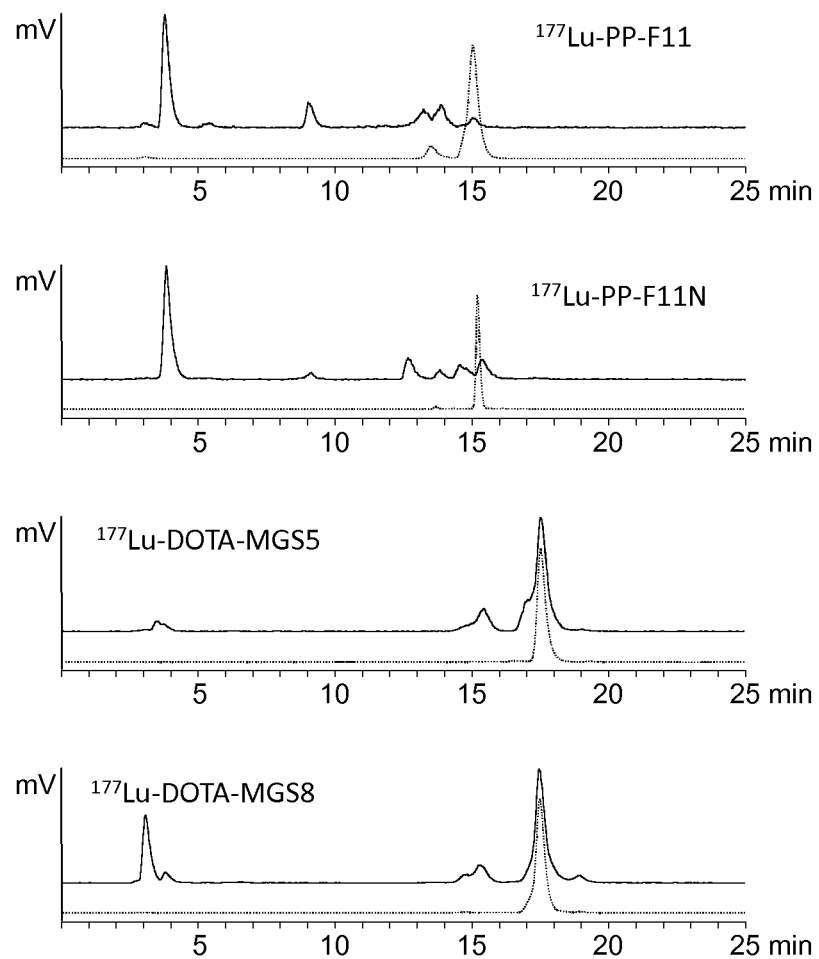

As shown in FIG. 6, the radiolabelled peptidomimetics of the present invention showed a very high stability against enzymatic degradation in vivo. The percentage of intact radioligand present in the blood at 10 min p.i. was ≥80% for all $^{111}$In-labelled peptidomimetics (n=2; $^{111}$In-DOTA-MGS5: 82.7±3.3%, $^{111}$In-DOTA-MGS5-2: 88.4±0.4%, $^{111}$In-DOTA-MGS8: 80.0±5.2%, $^{111}$In-DOTA-MGS9: 93.9±1.2%, $^{111}$In-DOTA-MGS10: 82.3±1.8%, $^{111}$In-DOTA-MGS11: 98.4±0.1%). The stability in vivo was considerably increased when compared to $^{111}$In-DOTA-MG11 showing only 5% intact radiopeptide 5 min after injection, whereas a similar improvement of in vivo stability was achievable only by coinjection the enzyme inhibitor phosphoramidon (Nock B A et al., J Nucl Med 2014, 55: 121-127). Further studies were performed also with selected $^{177}$Lu-labelled peptidomimetics (n=1) finding similar results. For $^{177}$Lu-DOTA-MGS5 the intact radioligand present in the blood amounted to 85.9% at 10 min p.i. and 77.0 at 30 min p.i., the values for $^{177}$Lu-DOTA-MGS8 resulted to be 80.5 and 56.8% at 10 and 30 min p.i., respectively.

For comparison, metabolic studies in vivo were carried out also with PP-F11 and PP-F11N labelled with Lu-177 (n=1).

PP-F11:
DOTA-DGlu-DGlu-DGlu-DGlu-DGlu-DGlu-Ala-Tyr-Gly-Trp-Met-Asp-Phe-NH$_2$

PP-F11N:
DOTA-DGlu-DGlu-DGlu-DGlu-DGlu-DGlu-Ala-Tyr-Gly-Trp-Nle-Asp-Phe-NH$_2$

All bonds ("-") in PP-F11 and PP-F11N are amide bonds and all amino acids whose enantiomeric form is not expressly indicated are in the L-form.

These two peptide derivatives are derived from MG0 by substitution of the penta-Glu sequence with five D-glutamic acid residues and additional substitution of Met with Nle in PP-F11N. The two peptide conjugates were developed with the aim to improve the metabolic stability and pharmacokinetics and were first described in 2012 (Kroselj M et al., Eur J Nucl Med Mol Imaging 2012, 39: S533-S534 and WO 2015/067473 A1). For the same time point at 10 min p.i., a low enzymatic stability was confirmed for $^{177}$Lu-PP-F11N with 22.3% intact radioligand present in the blood. At 30 min p.i. $^{177}$Lu-PP-F11 and $^{177}$Lu-PP-F11N showed values of 5.5 and 12.7%, respectively, and resulted to be almost completely degraded.

The peptidomimetics of the present invention therefore display a much higher stability against enzymatic degradation, as compared, for example, with PP-F11 and PP-F11N of the prior art. Surprisingly, the combination of substitutions in different positions, as according to the present invention, allows completely stabilizing the peptidomimetic.

Without being bound by any particular theory, it is currently believed that beside improved cellular uptake also the in vivo stability may contribute to the improved tumour uptake and retention. The extremely high tumour uptake and tumour retention as well as very favourable tumour-to-background activity ratios, including kidneys, render the present peptidomimetics particularly useful for diagnostic and therapeutic uses in CCK2R relevant diseases, such as cancer.

The invention claimed is:

1. A peptidomimetic comprising an amino acid polymer with the sequence
DGlu-Ala-Tyr-Gly-Trp-(N-Me)Nle-Asp-1Nal-NH$_2$,
DGlu-Ala-Tyr-Gly-Trp-(N-Me)Nle-Asp-2Nal-NH$_2$,
DGlu-Pro-Tyr-Gly-Trp-(N-Me)Nle-Asp-1Nal-NH$_2$,
DLys-Ala-Tyr-Gly-Trp-(N-Me)Nle-Asp-1Nal-NH$_2$,
DGlu-Tyr-Pro-Gly-Trp-(N-Me)Nle-Asp-1Nal-NH$_2$, or
DGlu-Ala-Tyr-Gly-Trp-(N-Me)Nle-Asp-(N-Me)1Nal-NH$_2$.

2. The peptidomimetic of claim 1, wherein the peptidomimetic is 8 to 13 amino acids in length.

3. The peptidomimetic of claim 1, wherein the peptidomimetic further comprises a reporter group or a cytotoxic group.

4. The peptidomimetic of claim 3, wherein the peptidomimetic further comprises a chelator and the reporter group or cytotoxic group is coordinated by the chelator, or wherein the peptidomimetic further comprises a prosthetic group and the reporter group or cytotoxic group is part of the prosthetic group.

5. The peptidomimetic of claim 3, wherein the reporter group or cytotoxic group is a radionuclide.

6. The peptidomimetic of claim 1 comprising an amino acid polymer with the sequence: DGlu-Ala-Tyr-Gly-Trp-(N-Me)Nle-Asp-1Nal-NH$_2$.

7. The peptidomimetic of claim 1 comprising an amino acid polymer with the sequence: DGlu-Ala-Tyr-Gly-Trp-(N-Me)Nle-Asp-2Nal-NH$_2$.

8. The peptidomimetic of claim 1 comprising an amino acid polymer with the sequence: DGlu-Pro-Tyr-Gly-Trp-(N-Me)Nle-Asp-1Nal-NH$_2$.

9. The peptidomimetic of claim 1 comprising an amino acid polymer with the sequence: DLys-Ala-Tyr-Gly-Trp-(N-Me)Nle-Asp-1Nal-NH$_2$.

10. The peptidomimetic of claim 1 comprising an amino acid polymer with the sequence: DGlu-Tyr-Pro-Gly-Trp-(N-Me)Nle-Asp-1Nal-NH$_2$.

11. The peptidomimetic of claim 1 comprising an amino acid polymer with the sequence: DGlu-Ala-Tyr-Gly-Trp-(N-Me)Nle-Asp-(N-Me)1Nal-NH$_2$.

12. A peptidomimetic consisting of the amino acid sequence:
DGlu-Ala-Tyr-Gly-Trp-(N-Me)Nle-Asp-1Nal-NH$_2$.

13. A pharmaceutical or diagnostic composition comprising the peptidomimetic of claim 1 and a pharmaceutical carrier.

14. A method of producing the peptidomimetic of claim 1, comprising synthesizing the peptidomimetic.

15. A method of delivering a reporter group or a cytotoxic group to a cell, comprising contacting a cell with the peptidomimetic of claim 3, wherein the peptidomimetic comprises a reporter group or a cytotoxic group, thereby delivering the reporter group or the cytotoxic group to the cell.

16. A method of imaging a cell that expresses CCK2R on the surface of the cell, wherein the method comprises the steps of
a) contacting the cell with the peptidomimetic of claim 1, wherein the peptidomimetic comprises a reporter group, and
b) visualizing the reporter group that is in contact with the cell.

17. The method of claim 16, wherein contacting comprises administering the peptidomimetic to a patient.

18. The method of claim 17, wherein the patient has cancer.

19. A method of treating a patient that suffers from a disease that involves the expression of CCK2R, comprising administering the peptidomimetic of claim 1 to the patient.

20. The method of claim 19, wherein the disease that involves expression of CCK2R is a cancer that expresses CCK2R on the surface of cancer cells.

21. The method of claim 19, wherein the disease that involves expression of CCK2R is thyroid cancer, lung cancer, gastrointestinal stromal tumors, tumors of the nervous system, stromal ovarian cancer, gastrointestinal cancer, neuroendocrine tumors, gastroenteropancreatic tumors, neuroblastoma, tumors of the reproductive system, insulinomas, vipomas, bronchial carcinoids, ileal carcinoids, leiomyosarcomas, leiomyomas, and/or granulosa cell tumors.

22. A method of diagnosing cancer that expresses CCK2R on the surface of a cancer cell in a patient, wherein the method comprises the steps of
a) contacting the cancer cell of the patient with the peptidomimetic of claim 1, wherein the peptidomimetic comprises a reporter group, and
b) visualizing the reporter group that is in contact with the cancer cell.

23. The method of claim 22, wherein the cancer is thyroid cancer, lung cancer, gastrointestinal stromal tumors, tumors of the nervous system, stromal ovarian cancer, gastrointestinal cancer, neuroendocrine tumors, gastroenteropancreatic tumors, neuroblastoma, tumors of the reproductive system, insulinomas, vipomas, bronchial carcinoids, ileal carcinoids, leiomyosarcomas, leiomyomas, and/or granulosa cell tumors.

* * * * *

UNITED STATES PATENT AND TRADEMARK OFFICE
CERTIFICATE OF CORRECTION

PATENT NO. : 12,049,518 B2
APPLICATION NO. : 16/620403
DATED : July 30, 2024
INVENTOR(S) : Von Guggenberg Zu Riedhofen et al.

It is certified that error appears in the above-identified patent and that said Letters Patent is hereby corrected as shown below:

In the Specification

Column 2, Line 9: Please correct "Metal.," to read --M et al.,--

Column 2, Line 61: Please correct "Metal.," to read --M et al.,--

Column 5, Line 19: Please correct "$^{111}$In-DOTA-MG11 $^{111}$In-PP-F11" to read --$^{111}$In-DOTA-MG11, $^{111}$In-PP-F11,--

Column 5, Line 26: Please correct "DOTA-MGS1" to read --DOTA-MGS10,--

Column 6, Line 49: Please correct "Glutamine (Gin);" to read --Glutamine (Gln);--

Column 7, Line 8: Please correct "(Ani)," to read --(Anl),--

Column 7, Line 15: Please correct "Metal.," to read --M et al.,--

Column 7, Line 16: Please correct "Metal.," to read --M et al.,--

Column 9, Line 12: Please correct "-CONCH-" to read -- -CONCH$_3$- --

Column 9, Line 24: Please correct "-CONCH-" to read -- -CONCH$_3$- --

Column 10, Line 38: Please correct "(C1-05)" to read --(C1-C5)--

Column 10, Line 56: Please correct "-CONCH-" to read -- -CONCH$_3$- --

Column 10, Line 62: Please correct "-CONCH-" to read -- -CONCH$_3$- --

Column 10, Line 66: Please correct "-CONCH-" to read -- -CONCH$_3$- --

Signed and Sealed this
Tenth Day of December, 2024

Katherine Kelly Vidal
*Director of the United States Patent and Trademark Office*

CERTIFICATE OF CORRECTION (continued)
U.S. Pat. No. 12,049,518 B2

Column 11, Line 3: Please correct "-CONCH-" to read -- -CONCH$_3$- --

Column 29, Lines 2-3: Please correct "[$^{125}$I]Tyr$^{12}$-gastrind" to read --[$^{125}$I]Tyr$^{12}$-gastrin-1--

Column 29, Lines 9-10: Please correct "[$^{125}$I]Tyr$^{12}$-gastrind" to read --[$^{125}$I]Tyr$^{12}$-gastrin-1--

Column 29, Line 48: Please correct "[$^{125}$I]Tyr$^{12}$-gastrind" to read --[$^{125}$I]Tyr$^{12}$-gastrin-1--

Column 32, Line 37: Please correct "Petal.," to read --P et al.,--